(12) United States Patent
Huang et al.

(10) Patent No.: US 9,617,302 B2
(45) Date of Patent: Apr. 11, 2017

(54) PEPTIDE COMPOUNDS FOR INHIBITION OF PLATELET AGGREGATION

(75) Inventors: Tur-Fu Huang, Taipei (TW);
Chien-Hsin Chang, Taipei (TW);
Ching-Hu Chung, Taipei (TW)

(73) Assignee: NATIONAL TAIWAN UNIVERSITY, Taipei (TW)

( * ) Notice: Subject to any disclaimer, the term of this patent is extended or adjusted under 35 U.S.C. 154(b) by 174 days.

(21) Appl. No.: 14/126,808

(22) PCT Filed: Jun. 14, 2012

(86) PCT No.: PCT/IB2012/001345
§ 371 (c)(1),
(2), (4) Date: Jul. 7, 2014

(87) PCT Pub. No.: WO2012/172427
PCT Pub. Date: Dec. 20, 2012

(65) Prior Publication Data
US 2014/0363423 A1    Dec. 11, 2014

Related U.S. Application Data

(60) Provisional application No. 61/496,742, filed on Jun. 14, 2011.

(51) Int. Cl.
| | | |
|---|---|---|
| A61K 38/08 | (2006.01) |
| A61K 45/06 | (2006.01) |
| C07K 7/06 | (2006.01) |
| C07K 7/08 | (2006.01) |
| C07K 7/64 | (2006.01) |
| C07K 14/705 | (2006.01) |
| A61K 38/00 | (2006.01) |

(52) U.S. Cl.
CPC ............ *C07K 7/06* (2013.01); *A61K 38/08* (2013.01); *A61K 45/06* (2013.01); *C07K 7/08* (2013.01); *C07K 7/64* (2013.01); *C07K 14/705* (2013.01); *A61K 38/00* (2013.01)

(58) Field of Classification Search
None
See application file for complete search history.

(56) References Cited

U.S. PATENT DOCUMENTS 6,075,129 A * 6/2000 Kini .................. C07K 7/08
530/326
6,284,475 B1    9/2001 Rand

FOREIGN PATENT DOCUMENTS

AT    WO2009149486 A2 * 12/2009 ............. A61K 38/08

OTHER PUBLICATIONS

NCBI WP_014067522.1. LPS biosynthesis protein [Rhodothermus marinus].*
NCBI WP_028391604.1. diaminopimelate decarboxylase [Bacillus cihuensis].*
Batuwangala T. et al., Structure of the snake-venom toxin convulxin. Acta crystallographica Section D, Jan. 2004;60(Pt 1):46-53.
Hooley E. et al., The crystal structure of the platelet activator aggretin reveals a novel (alphabeta) 2 dimeric structure, Biochemistry ,Jul. 29, 2008;47(30):7831-7.
Watson AA et al., Crystal structure of rhodocytin, a ligand for the platelet-activating receptor CLEC-2, Protein Sci., Sep. 2008;17(9):1611-6.
Yeh Chia-Hsin et al., Pharmacological characterization and antithrombotic effect of agkistin, a platelet glycoprotein Ib antagonist, British journal of pharmacology, Feb. 2001;132(4):843-850.
Chang CH. et al. The highly specific platelet glycoprotein (GP) VI agonist trowaglerix impaired collagen-induced platelet aggregation ex vivo through matrix metalloproteinase-dependent GPVI shedding, JJournal of Thrombosis and Haemostasis, Apr. 2008;6(4):669-676.

* cited by examiner

*Primary Examiner* — Satyanarayana R Gudibande
*Assistant Examiner* — Jia-Hai Lee
(74) *Attorney, Agent, or Firm* — Wpat, P.C., Intellectual Property Attorneys; Anthony King

(57) ABSTRACT

The invention relates to a peptide compound and its pharmaceutical composition for inhibiting platelet aggregation and preventing/treating thrombogenic diseases. The invention develops pentapeptides and hexapeptides derived from snake venom C-type lectin-like proteins (CLPs) fragments, which can inhibit platelet aggregation and have antithrombotic activity without hemorrhagic tendency. Accordingly, they can be used as potential agents for the prevention and therapy of thrombogenic diseases.

14 Claims, 14 Drawing Sheets

Fig. 2

α subunit

```
              1
Trowaglerix     DFKCPSEWYA  YDQHCYRIIN
Convulxin       GLHCPSDWYY  YDQHCYRIFN
Agglucetin      DFNCPPGWSA  YDQYCYQVIK
Alboaggregin A  DFHCLPGWSA  YDQYCYRVFN 21
Trowaglerix     KPQTWADAEK  F-PKQAKGG
Convulxin       EEMNWEDAEW  FCTKQAKGAH
Agglucetin      EPKNWDDAER  FCTEQADGGH
Alboaggregin A  EPKNWEDAER  FCAKQADSGH 41
Trowaglerix                         VTQN
Convulxin       LVSIKSAKEA  DFVAWMVTQN
Agglucetin      LVSIESKGER  DFVAQLVSQN
Alboaggregin A  LVSIETMGEA  DFVAQLISEN 61
Trowaglerix     IETPFHYVWI  GLRVQNKKQ
Convulxin       IEESFSHVSI  GLRVQNKEKQ
Agglucetin      IESVEDHVWT  GLRVQNKEKQ
Alboaggregin A  IQSEKHYVWI  GLKVQNKEQQ 81
Trowaglerix     CS
Convulxin       CSTKWSDGSS  VSYDNLLDLY
Agglucetin      CSTEWSDGSS  VSYENLLELY
Alboaggregin A  CSSEWSDGSS  VTYENLIKLY 101
Trowaglerix     NKPGALHQH   KGFCKWMNVA
Convulxin       ITKCSLLKKE  TGFRKWFVAS
Agglucetin      MRKCGALERE  TGFHKWINLG
Alboaggregin A  MRKCGALEQE  SGFRKWINLG 121
Trowaglerix     CAQKHPFVCK  FPPQCA
Convulxin       CIGKIPFVCK  FPPQC    46%
Agglucetin      CIQLNPFVCK  FPPQC    45%
Alboaggregin A  CIQLNPFVCK  FPPQ     44%
```

Fig. 5

(A) Collagen-induced aggregation

Troα $^{114-119}$ (Troα6):   CKWMNV
Troα6 scramble (s):   CWNKMV
Troα $^{112-121}$ (Troα10):   GFCKWMNVAC
Troα6 mutant (W116A):   CKAMNV
Troα6 mutant (M117A):   CKWANV
Troα6 mutant (W116A,M117A):   CKAANV Troα6 : CKWMNV
d-Troα6 : C(dK)WM(dN)V
Troα10 : GFCKWMNVAC
S1 : GFSKWMNVAC
S2 : GFCKWMNVAS
S1+2 : GFSKWMNVAS Troα10: GFCKWMNVAC
1: LFHVWPYWWW
2: LFHLWPYWWW
3: LFHVWDYYDR
4: LFHVWDYTDR

Fig. 7

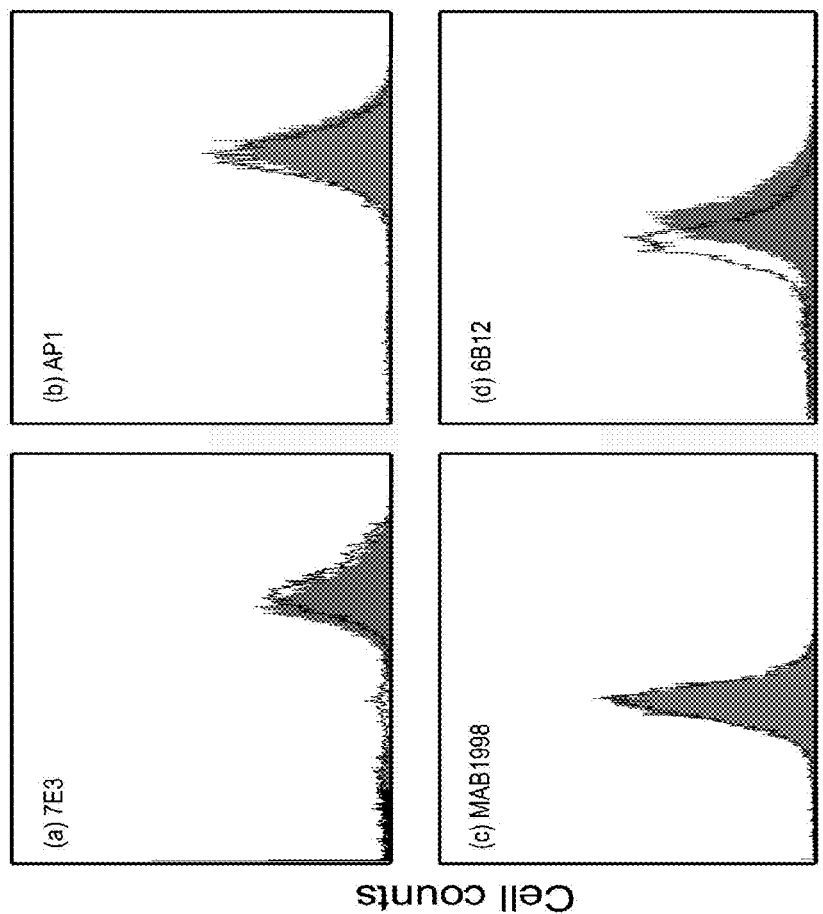
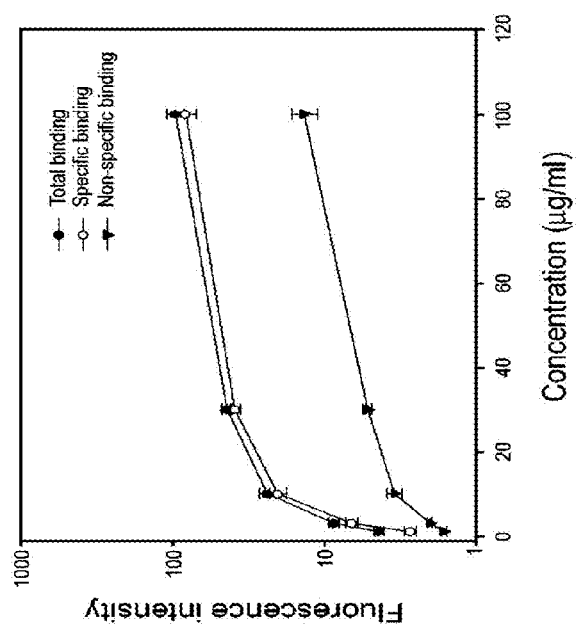
Fig. 10 (Continued)

PEPTIDE COMPOUNDS FOR INHIBITION OF PLATELET AGGREGATION

FIELD OF THE INVENTION

The invention provides a peptide compound and its pharmaceutical composition for inhibiting platelet aggregation and preventing/treating thrombogenic diseases. Particularly, the peptide compound is a pentapeptide or a hexapeptide.

BACKGROUND OF THE INVENTION

Appropriate platelet adhesion, activation and aggregation are important in maintaining a balance between normal hemostasis and pathological arterial thrombosis such as stroke and myocardial infarction. Exposure of matrix protein collagen after vessel injury provides a substrate for platelet adhesion and triggers platelet activation, which recruits additional platelets to area of injured vessel wall, thereby initiating thrombus formation. Platelet adhesion and aggregation are critical events in intravascular thrombosis. The formation of a blood clot is normally the result of tissue injury which initiates platelet adhesion/aggregation and coagulation cascade and has the effect of slowing or preventing blood flow in wound healing. However, in certain disease states the formation of blood clots within the circulatory system reaches an undesired extent and is itself the source of morbidity potentially leading to pathological consequences. Activated under conditions of turbulent blood flow in diseased vessels or by the release of mediators from other circulating cells and damaged endothelial cells lining the vessel, platelets accumulate at a site of vessel injury and recruit further platelets into the developing thrombus. The thrombus can grow to sufficient size to block off arterial blood vessels. Thrombi can also form in areas of stasis or slow blood flow in veins. Venous thrombi can easily detach portions of themselves called emboli that travel through the circulatory system and can result in blockade of other vessels, such as pulmonary arteries. Thus, arterial thrombi cause serious disease by local blockade, whereas venous thrombi do so primarily by distant blockade, or embolization. These conditions include venous thrombosis, thrombophlebitis, arterial embolism, coronary and cerebral arterial thrombosis, unstable angina, myocardial infarction, stroke, cerebral embolism, kidney embolisms and pulmonary embolisms.

Many adhesive proteins and various receptors are involved in the complex progress of platelet adhesion, activation and aggregation. Circulating platelets become adherent and form an occlusive thrombus either by exposure to atherosclerotic lesions following plaque rupture or in response to pathological shear stress. Integrin $\alpha 2\beta 1$ [glycoprotein (GP) Ia/IIa] and GPVI are two major platelet receptors for collagen, and mediate platelet adhesion and aggregation. Under high shear conditions, GPIb-V-IX complex is considered to be an indirect collagen receptor, acting through the binding of von Willebrand factor.

Snake venoms contain many biological components that affect hemostasis by various mechanisms, including affecting platelet function or coagulation factors, or disrupting endothelium. U.S. Pat. No. 6,284,475 uses this characteristic and provides methods for diagnosing and/or monitoring thrombophilic disease in a patient that can result from the antiphospholipid antibody syndrome (aPL syndrome), which are premised on the inhibition of binding of an anticoagulant protein, annexin, preferably annexin-V, to phospholipids by antiphospholipid (aPL) antibodies in a patient blood sample. C-type lectin-like proteins (CLPs) composed of $\alpha\beta$ heterodimers are an important family in snake venoms. CLPs are often oligomerized to form large molecules and interact with specific platelet receptors such as GPIb, $\alpha 2\beta 1$ or/and GPVI to activate or inhibit platelet function. Convulxin (CVX), a multimeric protein from *Crotalus durissus terrificus* venom, induces platelet activation via binding to GPVI and GPIb. The molecular interaction between convulxin and GPVI has been examined by X-ray crystallography, and the putative GPVI-binding sites of convulxin have been studied (Batuwangala T, Leduc M, Gibbins J M, et al. *Structure of the snake-venom toxin convulxin. Acta crystallographica* 2004 January; 60 (Pt 1):46-53). Aggretin, also known as rhodocytin, purified from *Calloselasma rhodostoma* venom, has been shown to bind to $\alpha 2\beta 1$, GPIb, and CLEC-2. Recently, the crystal structure of aggretin has been studied and its binding sites also have been proposed (Hooley E, Papagrigoriou E, Navdaev A, et al. *The crystal structure of the platelet activator aggretin reveals a novel (alphabeta) 2 dimeric structure. Biochemistry* 2008 Jul. 29; 47(30):7831-7; Watson A A, Eble J A, O'Callaghan C A. *Crystal structure of rhodocytin, a ligand for the platelet-activating receptor CLEC-2. Protein Sci* 2008 September; 17(9):1611-6). On the other hand, agkistin, purified from *Agkistrodon acutus* venom, inhibits platelet aggregation through its specific binding to platelet GPIb (Yeh C H, Chang M C, Peng H C, et al. *Pharmacological characterization and antithrombotic effect of agkistin, a platelet glycoprotein Ib antagonist. British journal of pharmacology* 2001 February; 132(4):843-5013). Trowaglerix, a CLPs purified from *Tropidolaemus waglerix* venom, specifically activates platelets via GPVI (Chang C H, Chung C H, Kuo H L, et al. *The highly specific platelet glycoprotein (GP) VI agonist trowaglerix impaired collagen-induced platelet aggregation ex vivo through matrix metalloproteinase-dependent GPVI shedding. J Thromb Haemost* 2008 April; 6(4):669-76). In a previous study, trowaglerix caused GPVI cleavage in vitro and abolished collagen-induced aggregation ex vivo. While the structure of CLPs together with their ligands have been determined, casting some light on the potential binding sites in a molecular level, the linear binding motif is also a very helpful indication for these binding ligands.

However, although the structure of CLPs together with their ligands have been determined, there is still a need to cast some light on the binding sites in a molecular level sp as to develop usable drugs with advantageous platelet aggregation inhibitory effect and antithrombotic activity without hemorrhagic tendency.

SUMMARY OF THE INVENTION

The invention provides a peptide compound comprising an amino acid sequence of formula $X_2$-Trp-$X_3$-$X_4$-$X_5$ (SEQ ID NO: 33), $X_1$-$X_2$-Trp-$X_3$-$X_4$-$X_5$ (SEQ ID NO: 34) or $X_1$-$X_2$-Trp-$X_3$-$X_4$ (SEQ ID NO: 35) or a pharmaceutically acceptable salt thereof, wherein $X_1$ is selected from the group consisting of: Arg (R), Lys (K), Gly (G), Ala (A), Val (V), Leu (L), Ile (I), Ser (S), Thr (T), Cys (C), Asn (N) and Gln (Q); $X_2$ is selected from the group consisting of: Lys (K), dLys (dK), Arg (R), Gly (G), Ala (A), Val (V), Leu (L), Ile (I), Ser (S), Thr (T), Cys (C), Gln (Q), Asn (N), Glu (E) and Asp (D); $X_3$ is selected from the group consisting of: Phe (F), Tyr (Y), Trp (W), Gly (G), Ala (A), Val (V), Leu (L), Ile (I), Ser (S), Thr (T), Cys (C), Met (M), Asn (N), Gln (Q), Glu (E) and Asp (D); $X_4$ is selected from the group consisting of: Gly (G), Ala (A), Val (V), Leu (L), Ile (I), Ser (S), Thr (T), Cys (C), Gln (Q) and Asn (N); and $X_5$ is selected from the group consisting of: Gly (G), Ala (A), Val (V), Leu (L), Ile (I), Ser (S), Thr (T), Cys (C), Phe (F), Tyr (Y), Trp (W), Met (M), Lys (K) and Arg (R).

The invention also provides a pharmaceutical composition, comprising a peptide compound of the invention, and a pharmaceutically acceptable excipient or carrier.

The invention further provides a method for inhibiting platelet aggregation, comprising administering an effective amount of a peptide compound or a pharmaceutical composition of the invention to a subject in need of such treatment.

The invention also further provides a method for the prevention or treatment of thrombogenic diseases, comprising administering an effective amount of a peptide compound or a pharmaceutical composition of the invention to a subject in need of such treatment.

BRIEF DESCRIPTION OF THE DRAWING

FIG. 2 shows the effects of CVX-α, or β C-terminal on the binding of AP1, MAB1998 or 6B12 Abs to platelet. Platelets ($3×10^7$ cells) were incubated with various concentrations of CVX-α, β C-terminal (thin line) or PBS (gray) for 30 min and then incubated with (A) Mab1998, (B) AP1 or (C) 6B12 Abs. After twice washout and incubation with secondary Abs, platelets were analyzed by flow cytometry. This is representative of three similar results.

Figure 11:
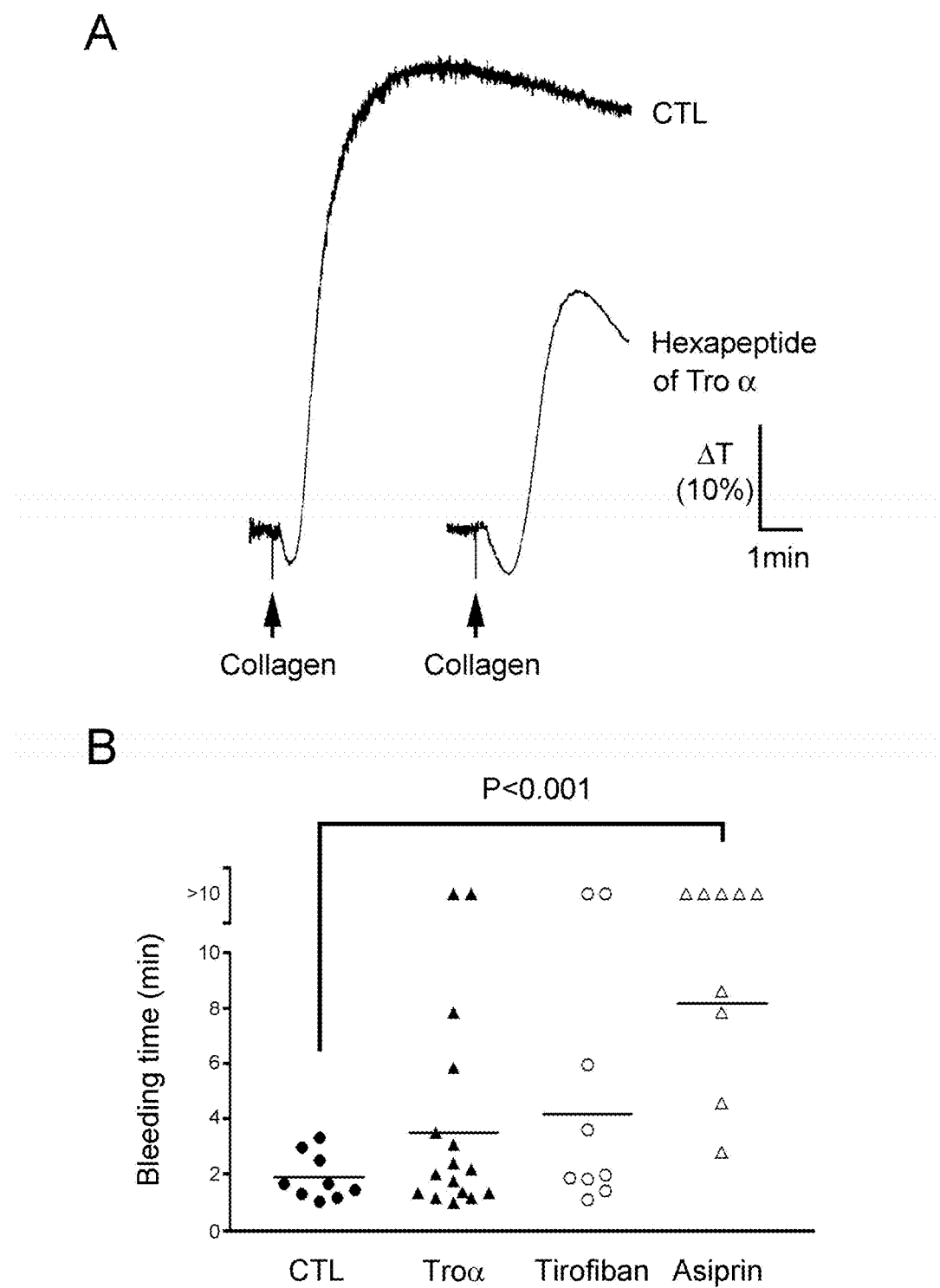

FIG. 11 shows effect of hexapeptide (Troα6) on collagen-induced platelet aggregation ex vivo (A) and tail bleeding in vivo (B). (A) The aggregation response of platelet-rich plasma (PRP) prepared from mice treated with PBS (CTL) or hexapeptide (Troα, 30 mg/kg) was initiated by the addition of collagen (3 μg/ml). This experiment is representative of at least six similar experiments. (B) Bleeding time was measured 5 min after the intravenous injection of (CTL), hexapeptide (Troα, 30 mg/kg), tirofiban (0.4 mg/kg), or aspirin (250 mg/kg). Bleeding time longer than 10 min was expressed as >10 min. The average bleeding time is indicated as (—). Each different symbol represents the bleeding time of the individual mouse.

Figure 12:
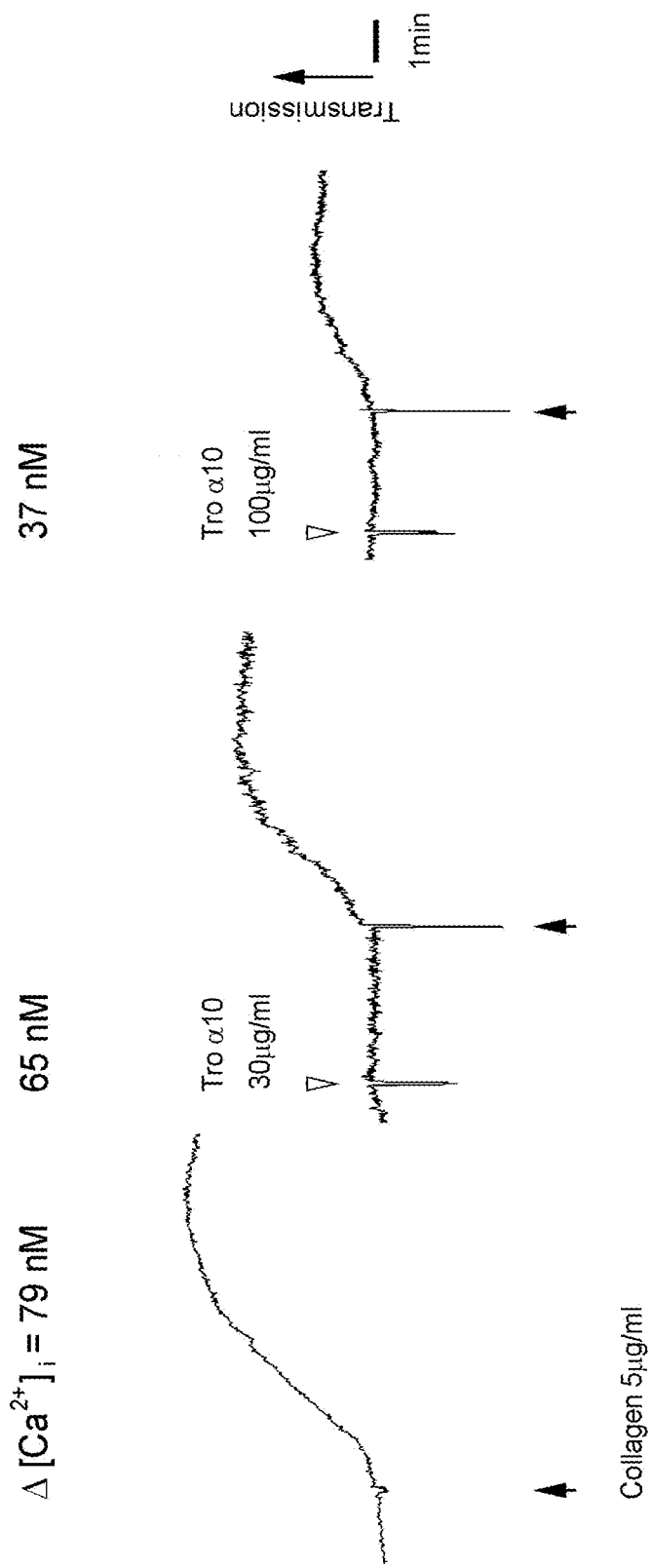

FIG. 12 shows binding target of synthetic peptides in human platelets. (A) Flow cytometric analysis of FITC-hexapeptide binding to platelets. Specific binding was calculated by subtracting the non-specific binding (probed by FITC-BSA) from total binding (probed by FITC-hexapeptide). (B) Washed platelets incubated with PBS (gray) or hexapeptide (thin line) were probed by anti-αIIbβ3 (7E3, a), anti-GPIb (AP1, b), anti-α2β1 (MAB1998, c), or anti-GPVI (6B12, d) mAbs. (C) Washed platelets incubated with PBS (thin line) or decapeptide (thick line) were probed by anti-α2β1 (6F1), anti-GPIb (6D1), or anti-GPVI (326E12) mAbs. After centrifugation, platelets were subjected to flow cytometric analysis by using FITC-conjugated anti-IgG mAbs. Results are presented as histograms of cell numbers versus fluorescence intensity. This experiment was repeated at least three times and only a representative tracing was shown.

DETAILED DESCRIPTION OF THE INVENTION

The invention first found that the snake venom C-type lectin-like proteins (CLPs) fragments serving as reactive sites with platelet glycoprotein locate at C-terminus. In view of this discovery, the invention develops pentapeptides and hexapeptides derived from these CLPs C terminus, which can inhibit platelet aggregation, in particular platelet aggregation caused by collagen, and have antithrombotic activity without hemorrhagic tendency. It is suggested that these peptides can be used as potential agents for the prevention and therapy of thrombogenic diseases.

DEFINITIONS

Unless otherwise specified, "a" or "an" means "one or more."

As used herein, "natural amino acid" means any of the twenty primary, naturally occurring amino acids which typically form peptides, polypeptides, and proteins. The following table is a tabulation of 20 naturally occurring amino acids.

| Naturally Occuring Amino Acids | | |
|---|---|---|
| Amino Acid | Three-letter Abbreviation | One-letter symbol |
| Alanine | Ala | A |
| Arginine | Arg | R |
| Asparagine | Asn | N |
| Aspartic Acid | Asp | D |
| Cysteine | Cys | C |
| Glutamine | Gln | Q |
| Glutamic Acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

As used herein, "synthetic peptide" means a compound of the invention conforming to the formulae mentioned herein, or a chemically modified amino acids, including but not limited to salts, derivatives (such as amides), and substitutions. The nomenclature used to define peptides herein is specified by Schroder & Lubke, "The Peptides," Academic Press, 1965, wherein, in accordance with conventional representation, the N-terminus appears to the left and the C-terminus to the right. Where an amino acid residue has isomeric forms, both the L-isomer form and the D-isomer form of the amino acid are intended to be covered unless otherwise indicated. Amino acids are commonly identified herein by the standard three-letter code. The D-isomer of an amino acid is specified by the prefix "D-" or "d". Similarly, the L-isomer is specified by the prefix "L-" or "l-." Peptides are represented herein according to the usual convention as amino acid sequences from left to right: N-terminus to C-terminus, unless otherwise specified.

As used herein, "conservative substitution" is the replacement of an amino acid with another amino acid that has the same net electronic charge and approximately the same size and shape. Amino acids with aliphatic or substituted aliphatic amino acid side chains have approximately the same size when the total number carbon and heteroatoms in their side chains differs by no more than about four. They have approximately the same shape when the number of branches in their side chains differs by no more than one. Amino acids with phenyl or substituted phenyl groups in their side chains are considered to have about the same size and shape. Listed below are five groups of amino acids. Replacing an amino acid in a polypeptide with another amino acid from the same group results in a conservative substitution: Group I: glycine, alanine, valine, leucine, isoleucine, serine, threonine, cysteine, and non-naturally occurring amino acids with $C_1$-$C_4$ aliphatic or $C_1$-$C_4$ hydroxyl substituted aliphatic side chains (straight chained or monobranched). Group II: glutamic acid, aspartic acid and non-naturally occurring amino acids with carboxylic acid substituted $C_1$-$C_4$ aliphatic side chains (unbranched or one branch point). Group III: lysine, ornithine, arginine and non-naturally occurring amino acids with amine or guanidino substituted $C_1$-$C_4$ aliphatic side chains (unbranched or one branch point). Group IV: glutamine, asparagine and non-naturally occurring amino acids with amide substituted $C_1$-$C_4$ aliphatic side chains (unbranched or one branch point). Group V: phenylalanine, phenylglycine, tyrosine and tryptophan.

As used herein, "highly conservative substitution" is the replacement of an amino acid with another amino acid that has the same functional group in the side chain and nearly the same size and shape. Amino acids with aliphatic or substituted aliphatic amino acid side chains have nearly the same size when the total number carbon and heteroatoms in their side chains differs by no more than two. They have nearly the same shape when they have the same number of branches in their side chains. Examples of highly conservative substitutions include valine for leucine, threonine for serine, aspartic acid for glutamic acid and phenylglycine for phenylalanine.

As used herein, "subject" refers to any animal including, but not limited to humans and other primates, rodents (e.g., mice, rats, and guinea pigs), lagamorphs (e.g., rabbits), bovines (e.g, cattle), ovines (e.g., sheep), caprines (e.g., goats), porcines (e.g., swine), equines (e.g., horses), canines (e.g., dogs), felines (e.g., cats), domestic fowl (e.g., chickens, turkeys, ducks, geese, other gallinaceous birds, etc.), as well as feral or wild animals, including, but not limited to, such animals as ungulates (e.g., deer), bear, lagamorphs, rodents, birds, etc. It is not intended that the term be limited to a particular age or sex. Thus, adult and newborn subjects, as well as fetuses, whether male or female, are encompassed by the term. Subjects "in need of treatment" are subjects with diseases and/or conditions that can be treated with platelet aggregation inhibitor or antithrombosis agent to achieve a beneficial therapeutic and/or prophylactic result. A beneficial outcome includes a decrease in the severity of symptoms or delay in the onset of symptoms, increased longevity and/or more rapid or more complete resolution of the disease or condition.

As used herein, "pharmaceutically acceptable" refers to compounds, materials, compositions, and/or dosage forms which are, within the scope of sound medical judgment, suitable for contact with the tissues of human beings and animals without severe toxicity, irritation, allergic response, or other complications, commensurate with a benefit-to-risk ratio that is reasonable for the medical condition being treated.

As used herein, "pharmaceutically acceptable salts" refer to derivatives of compounds wherein the parent compound is modified by making acid or base salts thereof.

As used herein, "effective amount" or "sufficient amount" of the synthetic peptide amide of the invention refers to an amount of the compound as described herein that may be therapeutically effective to inhibit, prevent, or treat a symptom of a particular disease, disorder, condition, or side effect.

The term "treat," "treatment" or "treating" means reducing the frequency, extent, severity and/or duration with a symptom of a particular disease, disorder, condition, or side effect.

The term "prevent," "prevention" or "preventing" means inhibition or the averting of symptoms of a particular disease, disorder, condition, or side effect.

New Peptides of the Invention

The invention found that the binding site with platelet glycoprotein at CLPs of snake venoms, convulxin (CVX), aggretin (Agg), agkistin (Agk) and trowaglerix (Tro) is located in C-terminus and the sequences at the binding sites of these CLPs have more than 50% similarity. The sequences of alpha-subunit of the CLPs of convulxin, aggretin, agkistin and trowaglerix and beta-subunit of the CLPs of convulxin are listed below.

```
Alpha-subunit of the CLPs

Convulxin    GLHCPSDWYY YDQHCYRIFN EEMNWEDAEW FCTKQAKGAH LVSIKSAKEA
(CVX)        DFVAWMVTQN IEESFSHVSI GLRVQNKEKQ CSTKWSDGSS VSYDNLLDLY
             ITKCSLLKKE TGFRKWFVAS CIGKIPFVCK FPPQC (SEQ ID NO: 1)

Aggretin     GLEDCDFGWS PYDQHCYQAF NEQKTWDEAE KFCRAQENGA HLASIESNGE
(Agg)        ADFVSWLISQ KDELADEDYV WIGLRAQNKE QQCSSEWSDG SSVSYENLID
             LHTKKCGALE KLTGFRKWVN YYCEQMHAFV CKLLPY (SEQ ID NO: 2)

Agkistin     DCLPGWSSYI RFCYQPFKLL KTWEDAERFC TEQANGGHLV SFESAREADF
             VAGVLSENIK IKPYVWIGLR VQNEGQQCSS KWSDSSKVSY ENLVEPFSKK
             CFVLKKDTGF RTWENVYCGL KHVFMCKYLK PR (SEQ ID NO: 3)

Trowaglerix  DFKCPSEWYA YDQHCYRIIN KPQTWADAEK FPKQAKGG-- ----------
(Tro)        -----VTQNI ETPFHYVWIG LRVQNKKKQC S--------- ----------
             NKPGALHQHK GFCKWMNVAC AQKHPFVCKF PPQCA (SEQ ID NO: 4)

Agglucetin   DFNCPPGWSA YDQYCYQVIKE PKNWDDAERF CTEQADGGHL VSIESKGERD
             FVAQLVSQNI ESVEDHVWTG LRVQNKEKQC STEWSDGSSV SYENLLELYM
             RKCGALERET GFHKWINLGC IQLNPFVCKF PPQC (SEQ ID NO: 5)

Beta-subunit of the CLPs

Convulxin    GFCCPSHWSS YDRYCYKVFK QEMTWADAEK FCTQQHTGSH LVSFHSTEEV
             DFVVKMTHQS LKSTFFWIGA NNIWNKCNWQ WSDGTKPEYK EWHEEFECLI
             SRTFDNQWLS APCSDTYSFV CKFEA (SEQ ID NO: 6)
```

On the basis of these sequences, the invention designs a number of short peptides.

In one aspect, the invention provides a peptide compound comprising an amino acid sequence of formula $X_2$-Trp-$X_3$-$X_4$-$X_5$ (SEQ ID NO: 36) or $X_1$-$X_2$-Trp-$X_3$-$X_4$ (SEQ ID NO: 37) or a pharmaceutically acceptable salt thereof, wherein $X_1$ is selected from the group consisting of: Arg (R), Lys (K), Gly (G), Ala (A), Val (V), Leu (L), Ile (I), Ser (S), Thr (T), Cys (C), Asn (N) and Gln (Q); $X_2$ is selected from the group consisting of: Lys (K), dLys (dK), Arg (R), Gly (G), Ala (A), Val (V), Leu (L), Ile (I), Ser (S), Thr (T), Cys (C), Gln (Q), Asn (N), Glu (E) and Asp (D); $X_3$ is selected from the group consisting of: Phe (F), Tyr (Y), Trp (W), Gly (G), Ala (A), Val (V), Leu (L), Ile (I), Ser (S), Thr (T), Cys (C), Met (M), Asn (N), Gln (Q), Glu (E) and Asp (D); $X_4$ is selected from the group consisting of: Tyr (Y), Gly (G), Ala (A), Val (V), Leu (L), Ile (I), Ser (S), Thr (T), Cys (C), Gln (Q) and Asn (N); and $X_5$ is selected from the group consisting of: Gly (G), Ala (A), Val (V), Leu (L), Ile (I), Ser (S), Thr (T), Cys (C), Phe (F), Tyr (Y), Trp (W), Met (M), Lys (K) and Arg (R).

In another aspect, the invention provides a peptide compound comprising an amino acid sequence of formula $X_1$-$X_2$-Trp-$X_3$-$X_4$-$X_5$ (SEQ ID NO: 38) or a pharmaceutically acceptable salt thereof, wherein $X_1$ is selected from the group consisting of: His (H), Arg (R), Lys (K), Gly (G), Ala (A), Val (V), Leu (L), Ile (I), Ser (S), Thr (T), Cys (C), Asn (N) and Gln (Q); $X_2$ is selected from the group consisting of: Lys (K), dLys (dK), Arg (R), Gly (G), Ala (A), Val (V), Leu (L), Ile (I), Ser (S), Thr (T), Cys (C), Gln (Q), Asn (N), Glu (E) and Asp (D); $X_3$ is selected from the group consisting of: Phe (F), Tyr (Y), Trp (W), Gly (G), Ala (A), Val (V), Leu (L), Ile (I), Ser (S), Thr (T), Cys (C), Met (M), Asn (N), Gln (Q), Glu (E) and Asp (D); $X_4$ is selected from the group consisting of: Tyr (Y), Gly (G), Ala (A), Val (V), Leu (L), Ile (I), Ser (S), Thr (T), Cys (C), Gln (Q) and Asn (N); and $X_5$ is selected from the group consisting of: Gly (G), Ala (A), Val (V), Leu (L), Ile (I), Ser (S), Thr (T), Cys (C), Phe (F), Tyr (Y), Trp (W), Met (M), Lys (K) and Arg (R).

According to the invention, pentapeptide with the formula $X_2$-Trp-$X_3$-$X_4$-$X_5$ (SEQ ID NO: 39) or $X_1$-$X_2$-Trp-$X_3$-$X_4$ (SEQ ID NO: 40) and hexapeptides with the formula $X_1$-$X_2$-Trp-$X_3$-$X_4$-$X_5$ (SEQ ID NO: 38) are synthesized on the basis of the sequences of C-terminal of snake venom CLPs.

According to the invention, $X_1$ is selected from the group consisting of: His, Arg, Lys, Gly, Ala, Val, Leu, Ile, Ser, Thr, Cys, Asn and Gln; $X_2$ is selected from the group consisting of: Lys, d-Lys, Arg, Gly, Ala, Val, Leu, Ile, Ser, Thr, Cys, Gln, Asn, Glu and Asp; $X_3$ is selected from the group consisting of: Phe, Tyr, Trp, Gly, Ala, Val, Leu, Ile, Ser, Thr, Cys, Met, Asn, Gln, Glu and Asp; $X_4$ is selected from the group consisting of: Tyr, Gly, Ala, Val, Leu, Ile, Ser, Thr, Cys, Gln, Asn and dAsn; and $X_5$ is selected from the group consisting of: Gly, Ala, Val, Leu, Ile, Ser, Thr, Cys, Phe, Tyr, Trp, Met, Lys and Arg. Preferably, $X_1$ is selected from the group consisting of: His, Arg, Cys, Asn and Thr; $X_2$ is selected from the group consisting of: Val, Lys, d-Lys, Cys, Thr, Gln and Glu; $X_3$ is selected from the group consisting of: Phe, Val, Met, Asn, Ala, Glu and Leu; $X_4$ is selected from the group consisting of: Tyr, Val, Asn, d-Asn and Ser; and $X_5$ is selected from the group consisting of: Ala, Tyr, Val, Met, Tyr and Arg.

In embodiments of the invention, the pentapeptide with the formula $X_2$-Trp-$X_3$-$X_4$-$X_5$ (SEQ ID NO: 41) is selected from the group consisting of: Lys-Trp-Met-Asn-Val (SEQ ID NO: 7), Lys-Trp-Val-Asn-Tyr (SEQ ID NO: 8), and Lys-Trp-Phe-Val-Ala (SEQ ID NO: 9). The pentapeptide with the formula $X_1$-$X_2$-Trp-$X_3$-$X_4$ (SEQ ID NO: 42) is selected from the group consisting of: Arg-Lys-Trp-Phe-Val (SEQ ID NO: 10), Arg-Lys-Trp-Val-Asn (SEQ ID NO: 11)_and Cys-Lys-Trp-Met-Asn (SEQ ID NO: 12). The hexapeptide with the formula $X_1$-$X_2$-Trp-$X_3$-$X_4$-$X_5$ (SEQ ID NO: 43) is selected from the group consisting of: Arg-Lys-Trp-Phe-Val-Ala (SEQ ID NO: 13), Arg-Lys-Trp-Val-Asn-Tyr (SEQ ID NO: 14), Cys-Lys-Trp-Met-Asn-Val (SEQ ID NO: 15), Cys-Trp-Asn-Lys-Met-Val (SEQ ID NO: 16), Cys-Lys-Ala-Met-Asn-Val (SEQ ID NO: 17), Cys-Lys-Trp-Ala-Asn-Val (SEQ ID NO: 18), Cys-Lys-Ala-Ala-Asn-Val (SEQ ID NO: 19), Cys-dLys-Trp-Met-dAsn-Val (SEQ ID NO: 20), Arg-Thr-Trp-Glu-Asn-Val (SEQ ID NO: 21), Asn-Gln-Trp-Leu-Ser-Ala (SEQ ID NO: 22), Thr-Glu-Trp-Leu-Asn-Met (SEQ ID NO: 23) and Asn-Gln-Trp-Leu-Ser-Arg (SEQ ID NO: 24).

In other embodiments of the invention, the hexapeptide $X_1$-$X_2$-Trp-$X_3$-$X_4$-$X_5$ (SEQ ID NO: 38) can further comprise one or more amino acid adjacent to $X_1$ and/or $X_5$. Preferably, it comprises about 1 to about 10 amino acids adjacent to $X_1$ and/or $X_5$; more preferably, about 1, 2, 3, 4, 5, 6, 7, 8, 9 or 10 amino acids. More preferably, it comprises about 1 or 2 amino acid(s) adjacent to $X_1$ and 1, 2, 3, or 4 amino acid(s) adjacent to $X_5$.

In a further embodiment, the peptide compound of the invention comprises an amino acid sequence of formula $X_1$-$X_2$-Trp-$X_3$-$X_4$-$X_5$-$B_1$-$B_2$ (SEQ ID NO: 44), $A_1$-$A_2$-$X_1$-$X_2$-Trp-$X_3$-$X_4$-$X_5$-$B_1$-$B_2$ (SEQ ID NO: 45), or $X_1$-$X_2$-Trp-$X_3$-$X_4$-$X_5$-$B_1$-$B_2$-$B_3$-$B_4$ (SEQ ID NO: 46), wherein $A_1$ is selected from the group consisting of: Gly, Ala, Val, Leu, Ile, Met, Phe, Trp and Pro; $A_2$ is selected from the group consisting of: Gly, Ala, Val, Leu, Ile, Met, Phe, Trp, Pro, Ser, Thr, Cys, Tyr, Asn and Gln; $B_1$ is selected from the group consisting of: Gly, Ala, Val, Leu, Ile, Met, Phe, Trp and Pro; $B_2$ is selected from the group consisting of: Ser, Thr, Cys, Tyr, Asn and Gln; $B_3$ is selected from the group consisting of: Gly, Ala, Val, Leu, Ile, Met, Phe, Trp and Pro; and $B_4$ is selected from the group consisting of: Ser, Thr, Cys, Tyr, Asn and Gln. For example, the peptide formula $X_1$-$X_2$-Trp-$X_3$-$X_4$-$X_5$-$B_1$-$B_2$ (SEQ ID NO: 44) comprises an amino acid sequence of: Cys-Lys-Trp-Met-Asn-Val-Ala-Cys (SEQ ID NO: 26). The peptide formula $X_1$-$X_2$-Trp-$X_3$-$X_4$-$X_5$-$B_1$-$B_2$-$B_3$-$B_4$ (SEQ ID NO: 46) comprises an amino acid sequence of: Gly-Phe-Cys-Lys-Trp-Met-Asn-Val-Ala-Cys (SEQ ID NO: 25) or Cys-Lys-Trp-Met-Asn-Val-Ala-Cys-Ala-Gln (SEQ ID NO: 27). The peptide formula $A_1$-$A_2$-$X_1$-$X_2$-Trp-$X_3$-$X_4$-$X_5$-$B_1$-$B_2$ (SEQ ID NO: 45) comprises an amino acid sequence of: Leu-Phe-His-Val-Trp-Asp-Tyr-Tyr-Asp-Arg (SEQ ID NO: 28) or Leu-Phe-His-Val-Trp-Asp-Tyr-Thr-Asp-Arg (SEQ ID NO: 29).

In another further embodiment, the peptide compound of the invention comprises an amino acid sequence of formula $A_1$-$A_2$-$X_1$-$X_2$-Trp-$X_3$-$X_4$-$X_5$-$B_1$-$B_2$-$B_3$-$B_4$ (SEQ ID NO: 47), wherein $A_1$ is absent or selected from the group consisting of: Gly, Ala, Val, Leu, Ile, Met, Phe, Trp and Pro; $A_2$ is selected from the group consisting of: Gly, Ala, Val, Leu, Ile, Met, Phe, Trp, Pro, Ser, Thr, Cys, Tyr, Asn and Gln; $B_1$ is selected from the group consisting of: Gly, Ala, Val, Leu, Ile, Met, Phe, Trp and Pro; $B_2$ is selected from the group consisting of: Ser, Thr, Cys, Tyr, Asn and Gln; $B_3$ is selected from the group consisting of: Gly, Ala, Val, Leu, Ile, Met, Phe, Trp and Pro; and $B_4$ is selected from the group consisting of: Ser, Thr, Cys, Tyr, Asn and Gln. For example, the peptide formula $A_1$-$A_2$-$X_1$-$X_2$-Trp-$X_3$-$X_4$-$X_5$-$B_1$-$B_2$-$B_3$-$B_4$ (SEQ ID NO: 47) comprises an amino acid sequence of: Gly-Phe-Cys-Lys-Trp-Met-Asn-Val-Ala-Cys-Ala-Gln (SEQ ID NO: 30).

According to the invention, each $A_1$ is absent or selected from the group consisting of: Gly, Ala, Val, Leu, Ile, Met, Phe, Trp and Pro; $A_2$ is selected from the group consisting of: Gly, Ala, Val, Leu, Ile, Met, Phe, Trp, Pro, Ser, Thr, Cys, Tyr, Asn and Gln; each $B_1$ is selected from the group consisting of: Gly, Ala, Val, Leu, Ile, Met, Phe, Trp and Pro; each $B_2$ is selected from the group consisting of: Ser, Thr, Cys, Tyr, Asn and Gln; each $B_3$ is selected from the group consisting of: Gly, Ala, Val, Leu, Ile, Met, Phe, Trp and Pro; and each $B_4$ is selected from the group consisting of: Ser, Thr, Cys, Tyr, Asn and Gln.

According to the invention, the amino acid residues mentioned herein cover both the L-isomer form and the D-isomer form unless otherwise indicated. The natural amino acids, with the exception of glycine, contain a chiral carbon atom. Unless otherwise specifically indicated, the optically active amino acids, referred to herein, are of the L-configuration. The stereochemistry at the carbon atom bearing the R substituent is either the D- or L-configuration. As is customary, the structure of peptides written out herein is such that the amino terminal end is on the left side of the chain and the carboxy terminal end is on the right side of the chain.

According to the invention, the peptide compound of the invention can be modified with peptide optimization. Preferably, the peptide of the invention is in the form of cyclic peptide or pseudocyclic peptide. The peptides of the invention can be conformationally restrained by cyclization of an amino acid residue side-chain onto a backbone amide bond replacement. The cyclization strategy may allow the preparation of a linear peptide of varying length containing a conformational restraint at the important sequence in the peptide such as Arg-Lys-Trp-Phe-Val, Arg-Lys-Trp-Val-Asn, Lys-Trp-Phe-Val-Ala, Lys-Trp-Val-Asn-Tyr, Cys-Lys-Val-Met-Asn, Lys-Trp-Met-Asn-Val and Cys-Lys-Trp-Met-Asn-Val etc. A combination of varying peptide length and localized conformational restraint may provide peptides with high platelet aggregation inhibiting activity. Linear peptides are generally flexible molecules with entropic limitations on achieving productive biologically active conformers. For this reason many authors have described the advantages of using various types of conformational and topographical constraints to reduce these degrees of freedom. Cyclic or pseudo-cyclic peptides may be prepared in which the ring is formed by oxidation of the naturally occurring cysteine residues yielding a disulfide bridged structure. In order to prepare cyclic or pseudo-cyclic peptides, the most common technique used to employ amino acids with orthogonally protected functional groups such that some are removable selectively in the presence of others. Those skilled in the art can use these techniques to prepare peptides in solution in which the amino terminus is cyclized to the carboxyl terminus to form a ring. Other means of forming cyclic or pseudo-cyclic peptides include side chain-to-side amide bonds or side chain-to-backbone linkages.

The peptide compounds of the invention also include pharmaceutically acceptable salts and derivatives of these peptides. Examples of pharmaceutically acceptable salts include, but are not limited to, mineral or organic acid salts of basic residues such as amines; alkali or organic salts of acidic residues such as carboxylic acids and the like. The pharmaceutically acceptable salts include the conventional non-toxic salts or the quaternary ammonium salts of the parent compound formed, for example, from non-toxic inorganic or organic acids. For instance, such conventional non-toxic salts include those derived from inorganic acids such as hydrochloric, hydrobromic, sulfuric, sulfamic, phosphoric, nitric acids and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic acids, and the like. These physiologically acceptable salts are prepared by methods known in the art, e.g., by dissolving the free amine bases with an excess of the acid in aqueous alcohol, or neutralizing a free carboxylic acid with an alkali metal base such as a hydroxide, or with an amine.

According to the invention, the derivatives of the peptides have modifications such as blocking groups (especially amidation at the C-terminus, but including, for example blocking groups on the C-terminus, N-terminus, and any charged side chains). Such groups may be added, for example, by amidation, esterification, and other means well known in the art. Examples of blocking groups are $NH_2$, lower alkyl or alkoxy($C_1$-$C_6$), lower alkyl carbonyl, lower alkenyl, lower alkynyl, formyl, lower aryl, aroyl, aryloxycarbonyl, aralkyloxy-carbonyl, lower alkyloxycarbonyl, phenyl, benzoyl, polyethylene glycol, nitro, —CN, saccharides, reduced carboxylates (i.e. aldehyde and alcohol), hydrazide, higher alkyl acylation (e.g. fatty acid acylation), biotinylation, and fluorescent labels. In all instances, "lower" refers to carbon chains having 1-6 carbon atoms. Persons of skill in the art will be familiar with the methods for making such modifications (see, e.g. Richard C. Larock, "Comprehensive Organic Transformations", 2nd Edition, published by Wiley-VCH. 1999.)

The peptides or their salts or derivatives can be chemically synthesized using standard chemical peptide synthesis techniques. For example, they can be synthesized by solid phase peptide synthesis (e.g., BOC or FMOC) method, by solution phase synthesis, or by other suitable techniques including combinations of the foregoing methods. The BOC and FMOC methods, which are established and widely used, are described in Merrifield, J. Am. Chem. Soc. 88:2149 (1963); Meienhofer, Hormonal Proteins and Peptides, C. H. Li, Ed., Academic Press, 1983, pp. 48-267; and Barany and Merrifield, in The Peptides, E. Gross and J. Meienhofer, Eds., Academic Press, New York, 1980, pp. 3-285. Methods of solid phase peptide synthesis are described in Merrifield, R. B., Science, 232: 341 (1986); Carpino, L. A. and Han, G. Y., J. Org. Chem., 37: 3404 (1972); and Gauspohl, H. et al., Synthesis, 5: 315 (1992)). The teachings of these articles are incorporated herein by reference in their entirety.

The peptides or their pharmaceutically acceptable salts or derivatives of the invention can inhibit platelet aggregation (in particular platelet aggregation caused by collagen) and have antithrombotic activity without hemorrhagic tendency, so they are potential agents for the prevention and therapy of thrombogenic diseases.

Pharmaceutical Compositions Comprising the Peptide Compound of the Invention

In another aspect, the invention provides a pharmaceutical composition, comprising a peptide compound of the invention, and a pharmaceutically acceptable excipient or carrier.

The peptide compounds of the invention can be incorporated into pharmaceutical compositions.

The compositions can include an effective amount of the peptide in a pharmaceutically acceptable excipient or carrier. Conventional excipients and/or, carriers for use in pharmaceutical compositions are generally inert and make up the bulk of the preparation.

The compositions of the present invention can be used as single agents (alone) or in combination(s) with a second active agent. In one embodiment, the second active agent is a Platelet aggregation inhibitor. These additional agents may include any one or number of the following drugs (including all of them): standard heparin, low molecular weight heparin, aspirin, ticlopidine, clopidogrel, abciximab, tirofiban, or eptifibatide.

The pharmaceutical compositions of the invention may be compounded according to conventional pharmaceutical techniques that will be familiar to persons of skill in the art. Physiologically acceptable carriers, excipients and stabilizers are described, for example in Remington's Pharmaceutical Sciences, 20.sup.th Ed. Mack Publishing Co. (2000). The carrier may be provided in a variety of forms depending on the form of preparation desired for administration. The peptide compounds and composition of the invention can be administered systemically or topically. The term systemic as used herein includes subcutaneous injection, intravenous, intramuscular, intrastemal injection, intravitreal injection, infusion, inhalation, transdermal administration, oral administration, rectal administration and intra-operative instillation. The followings are some examples of the compositions of the invention.

For oral delivery, the excipient or carrier formulation may contain inert customary ingredients or carriers such as sodium citrate or dicalcium phosphate and (a) binders, as for example, carboxymethylcellulose, alignates, gelatin, polyvinylpyrrolidone, sucrose, and acacia, (b) humectants, as for example, glycerol, (c) disintegrating agents, as for example, agar-agar, calcium carbonate, potato or tapioca starch, alginic acid, certain complex silicates, and sodium carbonate, (d) wetting agents, as for example, cetyl alcohol, and glycerol monostearate, (e) adsorbents, as for example, kaolin and bentonite, (f) fillers, such as lactose, starches, saccharides, sucrose, glucose, mannitol, and silicic acid, and (g) lubricants, as for example, magnesium stearate, talc, calcium stearate, solid polyethylene glycols, sodium lauryl sulfate, or mixtures thereof. These and other suitable pharmaceutically acceptable excipients are described in Remington's Pharmaceutical Sciences and in Handbook of Pharmaceutical Excipients, 3.sup.rd edition, Ed. Arthur H. Kibbe (American Pharmaceutical Association, Washington, D.C. 1999.

For parenteral administration, solutions of the peptide compounds of this invention in sesame or peanut oil, aqueous propylene glycol, or in sterile aqueous solutions may be employed. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, the sterile aqueous media employed are all readily available by standard techniques known to those skilled in the art. In intravenous administration, the compounds may be dissolved in appropriate intravenous delivery vehicles containing physiologically compatible substances, such as sterile sodium chloride having a buffered pH compatible with physiologic conditions, e.g. saline. Injectable suspension may also be prepared, in which case appropriate liquid carriers, suspending agents and the like may be employed.

For topical delivery, creams, gels, ointments or aerosols Ointments are typically prepared using an oleaginous base, e.g., containing fixed oils or hydrocarbons, such as white petrolatum or mineral oil, or an absorbent base, e.g., consisting of an absorbent anhydrous substance or substances, for example anhydrous lanolin. Following formation of the base, the active ingredients are added in the desired concentration.

Creams generally comprise an oil phase (internal phase) containing typically fixed oils, hydrocarbons, and the like, such as waxes, petrolatum, mineral oil, and the like, and an aqueous phase (continuous phase), comprising water and any water-soluble substances, such as added salts. The two phases are stabilized by use of an emulsifying agent, for example, a surface active agent, such as sodium lauryl sulfate; hydrophilic colloids, such as acacia colloidal clays, beegum, and the like. Upon formation of the emulsion, the active ingredients are added in the desired concentration.

Gels are comprised of a base selected from an oleaginous base, water, or an emulsion-suspension base, as previously described. To the base is added a gelling agent which forms a matrix in the base, increasing its viscosity to a semisolid consistency. Examples of gelling agents are hydroxypropyl cellulose, acrylic acid polymers, and the like. The active ingredients are added to the formulation at the desired concentration at a point preceding addition of the gelling agent.

For rectal delivery, suitable pharmaceutical compositions are, for example, topical preparations, suppositories or enemas. Suppositories are advantageously prepared from fatty emulsions or suspensions.

Applications

In other aspect, the invention provides a method for inhibiting platelet aggregation, comprising administering an effective amount of a peptide compound or a pharmaceutical composition of the invention to a subject in need of such treatment. Preferably, the platelet aggregation is that caused by collagen.

In a further aspect, the invention provides a method for the prevention and/or treatment of thrombogenic diseases, comprising administering an effective amount of a peptide compound or a pharmaceutical composition of the invention to a subject in need of such treatment.

The peptide compounds and pharmaceutical composition of the invention provide efficacy as antithrombotic agents by their ability to interact with GPVI and thus exhibit platelet aggregation inhibitory activity and antithrombotic activity. Moreover, peptide compounds and pharmaceutical composition of the invention do not cause hemorrhage. The peptide compounds and pharmaceutical compositions of the invention can be used for preventing or treating diseases or conditions associated with platelet aggregation and/or platelet activation. Accordingly, they can be used for preventing or treating thrombosis and related disorders, such as venous thrombosis, established peripheral arterial disease, thrombophlebitis, arterial embolism, coronary and cerebral arterial thrombosis, unstable angina, myocardial infarction, stroke, cerebral embolism, renal embolism, pulmonary embolism and other embolism- or thrombosis-related afflictions produced by but not limited to procedural or surgical interventions. This invention further provides methods for the prevention of embolism or thrombosis during percutaneous coronary interventions, placement of coronary stents, coronary angioplasty, coronary endarectomy, carotid endarectomy, or due to platelet-aggregation complications related to atherosclerosis, inflammation, exposure of blood to artificial devices, drug effects. This invention further provides methods for the prevention of sepsis (*Platelets Amplify Inflammation in Arthritis via Collagen-Dependent Microparticle Production* Eric Boilard et al. *Science* 327, 580 (2010)), tumor metastasis (*Platelet glycoprotein VI facilitates experimental lung metastasis in syngenic mouse models*. S. JAIN, S. RUSSELL, J. WARE. *Thromb Haemost.* 2009 October; 7(10):1713-7) and inflammatory arthritis (*Platelets: linking hemostasis and cancer*. Jain S, Harris J, Ware J. *Arterioscler Thromb Vasc Biol.* 2010 December; 30(12):2362-7).

The peptide compounds and pharmaceutical compositions of the invention are useful as anti-thrombotic agents, and are thus useful in the treatment or prevention of unstable angina, coronary angioplasty (PTCA) and myocardial infarction.

The peptide compounds and pharmaceutical compositions of the invention are useful in the treatment or prevention of primary arterial thrombotic complications of atherosclerosis such as thrombotic stroke, peripheral vascular disease, and myocardial infarction without thrombolysis.

The peptide compounds and pharmaceutical compositions of the invention are useful for the treatment or prevention of arterial thrombotic complications due to interventions in atherosclerotic disease such as angioplasty, endarterectomy, stent placement, coronary and other vascular graft surgery.

The peptide compounds and pharmaceutical compositions of the invention are useful for the treatment or prevention of thrombotic complications of surgical or mechanical damage such as tissue salvage following surgical or accidental trauma, reconstructive surgery including skin flaps, and "reductive" surgery such as breast reduction.

The peptide compounds and pharmaceutical compositions of the invention are useful for the prevention of mechanically-induced platelet activation in vivo, for example, caused by cardiopulmonary bypass, which results in temporary platelet dysfunction (prevention of microthromboembolism). The peptide compounds and pharmaceutical compositions of the invention are useful for prevention of mechanically-induced platelet activation in vitro. For example, the compounds are useful in the preservation of blood products, e.g. platelet concentrates, prevention of shunt occlusion such as renal dialysis and plasmapheresis, and thrombosis secondary to vascular damage/inflammation such as vasculitis, arteritis, glomerulonephritis and organ graft rejection.

The peptide compounds and pharmaceutical compositions of the invention are useful in disorders with a diffuse thrombotic/platelet consumption component such as disseminated intravascular coagulation, thrombotic thrombocytopenic purpura, hemolytic uremic syndrome, heparin-induced thrombocytopenia and pre-eclampsia/eclampsia.

The peptide compounds and pharmaceutical compositions of the invention are useful for the treatment or prevention of venous thrombosis such as deep vein thrombosis, veno-occlusive disease, hematological conditions such as thrombocythemia and polycythemia, and migraine The peptide compounds and pharmaceutical compositions of the invention are useful in treating a mammal to alleviate the pathological effects of atherosclerosis and arteriosclerosis, acute MI, chronic stable angina, unstable angina, transient ischemic attacks and strokes, peripheral vascular disease, arterial thrombosis, preeclampsia, embolism, restenosis or abrupt closure following angioplasty, carotid endarterectomy, and anastomosis of vascular grafts.

The peptide compounds and pharmaceutical compositions of the invention are useful in treating chronic or acute states of hyper-aggregability, such as disseminated intravascular coagulation (DIC), septicemia, surgical or infectious shock, post-operative and post-partum trauma, cardiopulmonary bypass surgery, incompatible blood transfusion, abruptio placenta, thrombotic thrombocytopenic purpura (TrP), snake venom and immune diseases, are likely to be responsive to such treatment.

The peptide compounds and pharmaceutical compositions of the invention are useful in treating diseases or conditions associated with platelet activation and/or aggregation produced by the contact of blood with an artificial device. In one embodiment, the artificial device is a paracorporeal artificial lung and an extracorporeal membrane oxygenation device. In another embodiment, the artificial device is an internal implantable artificial heart. In another embodiment, the artificial device is an apheresis instrument used to remove or isolate a specific component of the blood, and returning the remaining blood components to the donor. In yet another embodiment, the artificial device is a hemodialysis instrument.

The peptide compounds of the present invention are useful in vitro to inhibit the aggregation of platelets in blood and blood products, e.g. for storage, or for ex vivo manipulations such as in diagnostic or research use. In such applications, the compounds are administered to the blood or blood product.

In another preferred embodiment, the peptide compounds and pharmaceutical compositions of the invention are useful as adjunctive therapy in the prevention or treatment of thrombotic disorders, such as coronary arterial thrombosis during the management of unstable angina, coronary angioplasty and acute myocardial infarction, i.e. perithrombolysis. The peptide compounds and pharmaceutical compositions of the invention are administered in combination with other antiplatelet and/or anticoagulant drugs such as heparin, aspirin, dipyrimamole, cilostazol, GP IIb/IIIa antagonists, or thrombin inhibitors.

Other applications of peptide compounds and pharmaceutical compositions of the invention include prevention of platelet thrombosis, thromboembolism and reocclusion during and after thrombolytic therapy and prevention of platelet thrombosis, thromboembolism and reocclusion after angioplasty of coronary and other arteries and after coronary artery bypass procedures.

The peptide compounds and compositions of the invention can be administered by any suitable route, locally or systemically, including, for example, by parenteral administration. Parenteral administration can include, for example, intramuscular, intravenous, subcutaneous, or intraperitoneal injection. Topical administration can include, for example, creams, gels, ointments or aerosols. Respiratory administration can include, for example, inhalation or intranasal drops.

The amount of peptide compound and compositions administered will depend on the degree, severity, and type of the disease or condition, the amount of therapy desired, and the release characteristics of the pharmaceutical formulation. It will also depend on the subject's health, size, weight, age, sex and tolerance to drugs. Typically, the peptide or composition is administered for a sufficient period of time to achieve the desired therapeutic effect.

Publications cited herein are hereby incorporated by reference.

While the invention has been described in detail, and with reference to specific embodiments thereof, it will be apparent to one of ordinary skill in the art that various changes and modifications can be made therein without departing from the spirit and scope thereof

EXAMPLE

The following experimental examples are provided in order to demonstrate and further illustrate various aspects of certain embodiments of the present invention and are not to be construed as limiting the scope thereof. In the experimental disclosure which follows, the following materials and methods are used:

Materials

Trowaglerix was purified from *Tropidolaemus waglerix* venom as previously described (Chang C H, Chung C H, Kuo H L, et al. *The highly specific platelet glycoprotein (GP) VI agonist trowaglerix impaired collagen-induced platelet aggregation ex vivo through matrix metalloproteinase-dependent GPVI shedding. J Thromb Haemost* 2008 April; 6(4):669-76). Heparin was from Novo Nordisk A/S (Bagsvaerd, Denmark). PGE1, tris-(hydroxymethyl) aminomethane (Tris), dithiothreitol (DTT), indomethacin and ethylenediamine-tetra-acetic acid (EDTA) were obtained commercially from Sigma Chemical Co. (St. Louis, Mo., USA). Cyanogens bromide (CNBr) was purchased from Hayashi Pure Chemical Ltd. (Osaka, Japan). Monoclonal antibody (mAb) AP1 against GPIb was kindly supplied by Dr. Robert Montgomery (The Blood Center of Southeastern Wisconsin, Milwaukee, Wis., USA). 6B12 anti-GPVI mAb was kindly donated by B. Boylan (The Blood Center, Milwaukee, Wis., USA). Anti-α2β1 mAb (MAB1998) was purchased from Chemicon (Temecula, Calif., USA). FITC-conjugated goat anti-mouse IgG was purchased from Santa Cruz Biotechnology, Inc. (CA, USA).

Methods

Bacterial Expression of Specific Fragment of Snake CLPs

In-frame fusions of specific DNA fragment coding for CVX α, β C-terminal was polymerase chain reaction (PCR)-amplified by overlap extension and inserted into the pET31b (+) expression vector. For pGEX-2T system, two synthetic primers were designed with a cohesive end, NdeI site and XhoI site. PCR products were cleaved with the restriction enzymes (NdeI and XhoI site), purified, and ligated with T4 DNA ligase into the large fragment of NdeI and XhoI site cut pET31b(+) vector. The final constructs were verified by sequencing. Supplementary data are available at Protein Engineering online. Bacterial expression vectors were transformed into E. coli cells BL21 (DE3). The expression of the snake CLPs fragment was done in the presence of 0.1 mM isopropylthiogalactopyranoside (IPTG) at 37° C. After cell harvest and centrifugation, the cell pellet was suspended in PBS (150 mM NaCl, 10 mM $Na_2HPO_4$, pH 7.4) containing 5 mM dithiotreitol and 1 g/L lysozyme. After a 45-min-incubation on ice, the cells were disrupted in a Sonifier II disrupter (Branson Ultrasonic, Carouge-Geneva, Switzerland) by a maximum of 3 pulses of 10 sec each, avoiding frothing. The sonicated solution was incubated in the presence of 1% Triton X-100 for 1 hour at 4° C. with slight agitation. The homogenate was then centrifuged at 14000 rpm for 30 min at 4° C. The solution was centrifuged to remove particulate matter and the supernatant was applied to a HIS-Select Nickel Affinity Gel (SIGMA). The recombinant snake CLPs were eluted with elution buffer. The eluted products were analyzed by 20% reduced and non-reduced SDS-PAGE.

Site-Directed Mutagenesis

CVX α and β C-terminal mutations were generated using QuikChange Site-Directed Mutagenesis system (Stratagene, USA). Plasmid template DNA (approximately 0.5 pmole) was added to a PCR cocktail containing, in 25 ul of 1× mutagenesis buffer: (20 mM Tris HCl, pH 7.5; 8 mM $MgCl_2$; 40 ug/ml BSA); 12-20 pmole of each primer (one of which must contain a 5-prime phosphate), 250 uM each dNTP, 2.5 U Taq DNA polymerase, 2.5 U of Taq Extender (Stratagene). The PCR cycling parameters were 1 cycle of: 4 min at 94° C., 2 min at 50° C. and 2 min at 72° C.; followed by 5-10 cycles of 1 min at 94° C., 2 min at 54° C. and 1 min at 72° C. The parental template DNA and the linear, mutagenesis-primer incorporating newly synthesized DNA were treated with DpnI (10 U) and Pfu DNA polymerase (2.5 U). This results in the DpnI digestion of the in vivo methylated parental template and hybrid DNA and the removal, by Pfu DNA polymerase, of the Taq DNA polymerase-extended base(s) on the linear PCR product. The reaction was incubated at 37° C. for 30 min and then transferred to 72° C. for an additional 30 min. Mutagenesis buffer (lx, 115 ul, containing 0.5 mM ATP) was added to the DpnI-digested, Pfu DNA polymerase-polished PCR products. The solution was mixed and 10 ul was removed to a new microfuge tube and T4 DNA ligase (2-4 U) was added. The ligation was incubated for more than 60 min at 37° C. The treated solution was transformed into competent E. coli.

Digestion of Alkylated Trowaglerix with CNBr

The separation of subunits of alkylated trowaglerix was prepared according to the previously described protocol (Chang C H, Chung C H, Kuo H L, et al. *The highly specific platelet glycoprotein (GP) VI agonist trowaglerix impaired collagen-induced platelet aggregation ex vivo through matrix metalloproteinase-dependent GPVI shedding. J Thromb Haemost* 2008 April; 6(4):669-76). Separated subunits were further dissolved in 70% formic acid and reacted with CNBr at room temperature overnight. Formic acid and CNBr were removed by vacuum-drying. The CNBr-cleaved fragments of S-pyridylethylated trowaglerix were subjected to reverse-phase high-performance liquid chromatography (HPLC) on a C8 column (3.9×150 mm, Waters) using an acetonitrile gradient in 0.1% trifluoroacetic acid (TFA).

Peptide Synthesis

Several peptides based on the sequences of snake venom CLPs, including aggretin (Agg), convulxin (CVX), trowaglerix (Tro) and agkistin (Agk) (Chen Y L, Tsai K W Chang T, et al. *Glycoprotein Ib-binding protein from the venom of Deinagkistrodon acutus—cDNA sequence, functional characterization, and three-dimensional modeling. Thrombosis and haemostasis* 2000 January; 83(1):119-26; Chung C H, Au L C, Huang T F. *Molecular cloning and sequence analysis of aggretin, a collagen-like platelet aggregation inducer. Biochemical and biophysical research communications* 1999 Oct. 5; 263(3):723-7) were synthesized by MDBio, Inc. FITC-conjugated hexapeptide was commercially obtained from MDBio, Inc. Snake venom CLPs have been widely used to study platelet receptors, and some of their crystal structures have been studied. According to the putative binding sites of CLPs, we synthesized several hexapeptides or decapeptide of CLPs of C-terminus to examine their effects on platelet functions.

Preparation of Human Platelet-Rich Plasma and Platelet Suspension and Platelet Aggregation Assay Blood was collected from healthy human volunteers, who did not take any medication within 2 weeks before the study, and anticoagulated with acid citrate dextrose or 3.8% sodium citrate (9:1, v/v). After centrifugation at 100 g at room temperature for 9 min to obtain platelet-rich plasma (PRP), and platelet suspensions were prepared according to the previously described protocol (Mustard J F, Perry D W, Ardlie N G, et al. *Preparation of suspensions of washed platelets from humans. British journal of haematology* 1972 February; 22(2): 193-204). Platelet aggregation was measured with an aggregometer (Payton Scientific, Buffalo, N.Y., USA) under continuous stirring at 900 rpm at 37° C. The extent of platelet aggregation was continually monitored and expressed as increase in light transmission at 5 min after the addition of aggregation agonist.

Measurement of Thromboxane B2 Formation

Thromboxane $B_2$ formation of platelets induced by collagen was terminated by adding indomethacin (50 μM) and EDTA (2 mM) at 6 min following the addition of test sample. Hexapeptide was preincubated with platelets 3 min prior to the addition of inducer. After centrifugation at 14,000 rpm for 2 min, the content of thromboxane $B_2$, a stable metabolite of thromboxane $A_2$, in the supernatant was determined by $TxB_2$ enzyme immunoassay (EIA) kit (Amersham Pharmacia, Sweden).

Flow Cytometry Analysis of P-Selectin Expression

P-selectin expression on the cell surface of platelets was measured by flow cytometry. Washed platelets were prepared as above and adjusted to $3\times10^8$ platelets/ml. Washed platelets were pretreated with 100 ng/ml Aggrastat to prevent platelet aggregation, then 5 μg/ml collagen was added for 5 min, and finally anti-CD62P-FITC was added and incubated for 15 min. The resulting platelets were analyzed by flow cytometer. Hexapeptide was preincubated with platelets 3 min prior to the addition of collagen.

Measurement of the Intracellular Ca$^{2+}$ Level

The concentration of intracellular free Ca$^{2+}$ was determined using a fluorescent probe, Fura-2/AM, according to the method of Pollock and Rink (Pollock W K, Rink T J. *Thrombin and ionomycin can raise platelet cytosolic Ca2+ to micromolar levels by discharge of internal Ca2+ stores: studies using fura-2. Biochemical and biophysical research communications* 1986 Aug. 29; 139(1):308-14). Fura-2/AM—loaded platelets were prepared as the washed platelets except washing with Ca$^{2+}$-free Tyrode solution and allowed platelets to uptake Fura-2/AM (5 µM) for 30 min in the first wash. The intracellular Ca$^{2+}$ level of Fura-2-loaded platelets (3×10$^8$/ml) in the presence of 1 mM of Ca$^{2+}$ was measured by the fluorescence change (excitation at 339 nm, emission at 500 nm) with a Hitachi fluorescence spectrophotometer. The intracellular Ca$^{2+}$ concentration was calculated by the equation described by Grynkiewicz et al. (Grynkiewicz G, Poenie M, Tsien R Y. *A new generation of Ca2+ indicators with greatly improved fluorescence properties. J Biol Chem* 1985 Mar. 25; 260(6):3440-50).

Flow Cytometry Analysis of Binding Assay

Washed platelets (3×10$^8$ platelets/ml) containing 2 µM PGE1 were incubated with hexapeptide of trowaglerix α subunit (100 µg/ml) at room temperature for 30 min. Following incubation, plaetelets were labeled with primary anti-GPIb, α2β1 integrin, 0E1133 or GPVI mAbs (10 µg/ml) at room temperature for 15 min. Labeled cells were washed and then incubated with secondary FITC-conjugated goat anti-mouse IgG at room temperature for 15 min, and then analyzed immediately by FACS Calibur (Becton Dickinson, USA) using excitation and emission wavelength at 488 and 525 nm, respectively. Fluorescence signals from 10,000 cells were collected to calculate mean florescence intensity of a single cell. In addition, we used FITC-hexapeptide as a probe to evaluate direct binding of hexapeptide. Washed platelets (3×10$^8$ platelets/ml) containing 2 µM PGE1 were incubated with various concentration of FITC-hexapeptide or FITC-BSA (as a negative control) at room temperature for 15 min, and then analyzed immediately by FACS.

Ex Vivo Platelet Aggregation Study

Male ICR mice (25-30 g) were intravenously (IV) injected with PBS or hexapeptide (30 mg/kg), and then blood was collected at 5 min after injection. The platelet number of the whole blood sample was counted by a Sysmex cell counter (Chuo-Ku Kobe, Japan). PRP was prepared immediately by centrifugation at 200 g for 5 min. Platelet counts in PRP were adjusted to 3×10$^8$/ml and aggregation assay was performed in an aggregometer.

Fluorescein Sodium-Induced Platelet Thrombus Formation in Mesenteric Vunules of Mice Platelet plug formation in mesenteric microvessels was performed according to a previously described method with modification (Chang M C, Lin H K, Peng H C, et al. *Antithrombotic effect of crotalin, a platelet membrane glycoprotein Ib antagonist from venom of Crotalus atrox. Blood* 1998 Mar. 1; 91(5):1582-9). In brief, male ICR mice (12-14 g) were anesthetized with sodium pentobarbital (50 mg/kg) by intraperitoneal (IP) injection, and then the fluorescein sodium (12.5 mg/kg) was IV injected into a lateral tail vein of the mouse. After exteriorizing the small intestine, a mesenteric membrane with a microvascular bed was placed on a transparent plastic plate for microscopic observation. To prevent the mesentery from drying out, continuous rinsing of the mesentery with warm isotonic saline kept at 37° C. was performed. Venules with diameters of 30-40 µm were selected to be irradiated to produce a microthrombus. In the epi-illumination system, the area of irradiation (wavelength above 520 nm) was approximately 50 µm in diameter on the focal plane. After the operation (10 min), the mouse was IV injected with PBS (control), aspirin (150 mg/kg), or hexapeptide (30 mg/kg) through other lateral tail vein. Five min after administration of these drugs, the irradiation by filtered light was started and the occlusive time (upon cessation of blood flow) was recorded.

Tail Bleeding Time in Mice

Bleeding time was measured by a minor modified method described by Dejana et al (Dejana E, Villa S, de Gaetano G. *Bleeding time in rats: a comparison of different experimental conditions. Thrombosis and haemostasis* 1982 Aug. 24; 48(1):108-11). PBS or hexapeptide (30 mg/kg) was injected intravenously through a tail vein of the mouse (ICR, male, 25-30 g). A sharp cut of 2 mm from tail tip of mouse was made 5 min after injection. The tail was immediately placed into a tube filled with saline, kept at 37° C. for measuring bleeding time.

Statistical Analysis

All values are presented as mean±SEM. Differences between groups were assessed by one-way ANOVA and Newman-Keuls multiple comparison test where appropriate. P values less than 0.05 (P<0.05) were considered as significant difference.

Example 1

Inhibitory Effect of Recombinant Convulxin C-Terminal on Platelet Aggregation

Figure 1:
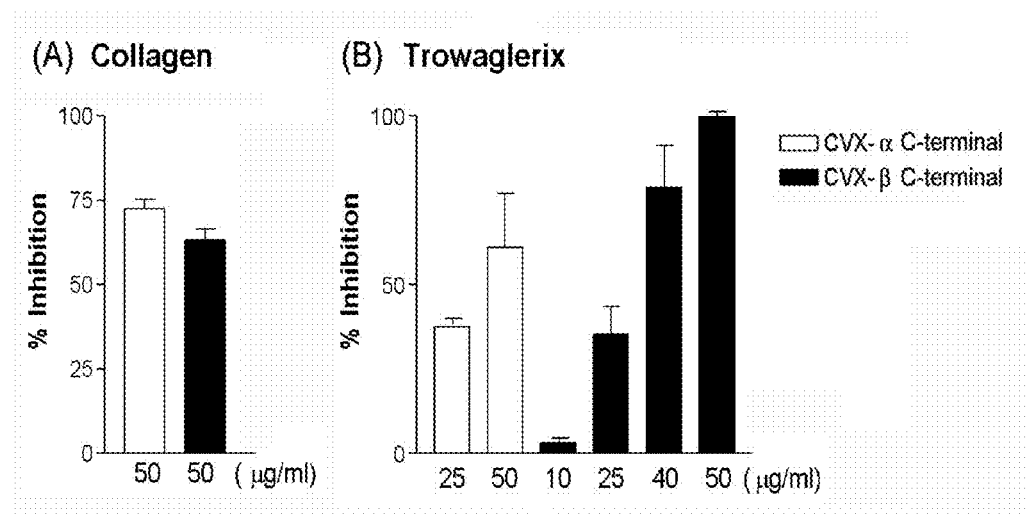
FIG. 1 shows the inhibitory effect of recombinant convulxin C-terminal on platelet aggregation. Washed platelet were preincubated with various concentrations of recombinant C-terminal of convulxin α, or β subunit at 37□ for 3 min, and then (A) collagen (2 μg/ml) or (B) trowaglerix (10 ng/ml) was added for induction of platelet aggregation. Results are expressed as percentage of inhibition. Data are presented as mean±SEM (n≥3).

Pretreatment of CVX α or β C-terminal (CVX α □C-terminal$^{104-135}$: □ CSLLKKETGFRKWFVASCIGKIPFVCK-FPPQC (SEQ ID NO: 31), CVX β C-terminal$^{94-125}$: EEFE-CLISRTFDNQWLSAPCSDTYSFVCKFEA (SEQ ID NO: 32), 50 µg/ml) significantly inhibited collagen-induced platelet aggregation (FIG. 1A). Since collagen may interact with receptors, integrin α2β1 and GPVI, the specificity and binding affinity of the CLPs fragments toward these receptors may be different. Trowaglerix, a GPVI agonist, and ristocetin, an indirect GPIb agonist were also used as aggregation agonist to test the inhibitory effects of CVX α, β C-terminal (Chang C H, Chung C H, Kuo H L, et al. *The highly specific platelet glycoprotein (GP) VI agonist trowaglerix impaired collagen-induced platelet aggregation ex vivo through matrix metalloproteinase-dependent GPVI shedding. J Thromb Haemost* 2008 April; 6(4):669-76; Sweeney J D, Labuzetta J W, Bernstein Z P, et al. *Ristocetin-induced platelet aggregate formation and adherence to the probe of an impedance aggregometer. Am J Clin Pathol* 1990 April; 93(4):548-51). Both CVX α, and β subunit C-terminal showed a concentration-dependent, and profound inhibition on trowaglerix-induced platelet aggregation (10-90% inhibition) (FIG. 1B). Interestingly, CVXα, and β C-terminal at 50 µg/ml abolished collagen-induced platelet aggregation, only had slight inhibitory effect (about 20%) on ristocetin-induced platelet activation (data not shown). These results indicate that CVXα, and β C-terminals may be responsible for CVX binding toward GPVI or α2β1 integrin.

Example 2

Effects of CVX-α, or β C-Terminal on the Binding of MAB1998, AP1 or 6B12 Abs to Platelet To study the target site of CVX-α, or β C-terminal on platelets, platelets were incubated with CVX-α, or β C-terminal and various antibodies to examine the binding reaction. The binding of anti-integrin α2β1 mAb, MAB1998 and a mAb against GPIb, AP1, were not affected by CVX-α, or β C-terminal (FIG. 2A, B). In contrast, CVX-α, or β C-terminal significantly inhibited the binding of anti-GPVI Ab, 6B12 to platelets (FIG. 2C). These results indicate that the binding target of CVX α, or β C-terminal is GPVI.

Example 3

Inhibitory Effect of Recombinant or Mutant Convulxinα, or β Subunit C-Terminal

Figure 3:
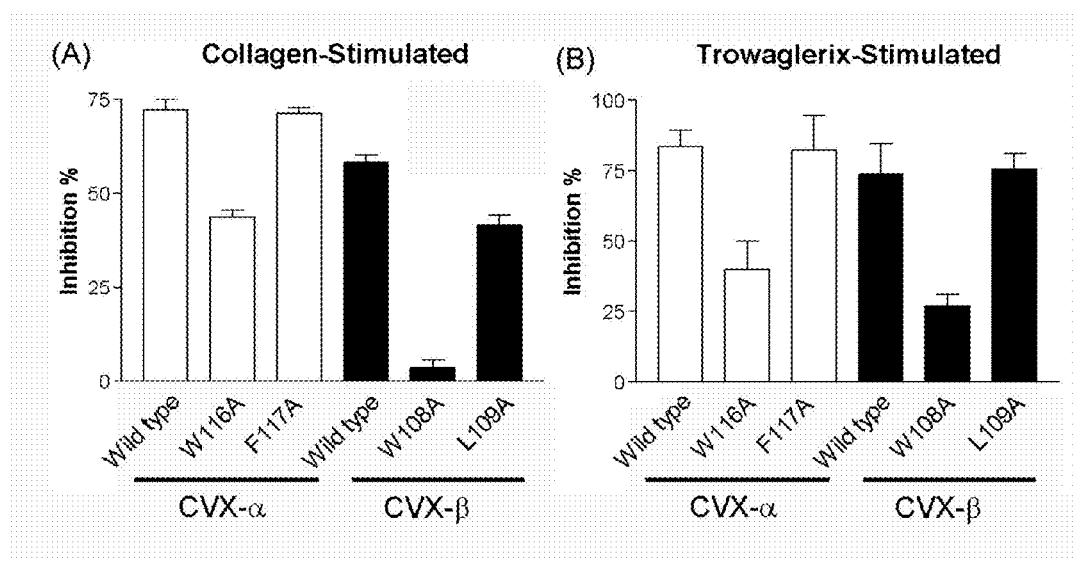
FIG. 3 shows the inhibitory effect of recombinant or mutant convulxin α, β subunit C-terminal on collagen or trowaglerix-induced platelet aggregation. Washed platelets were preincubated with wild type of convulxin α, β subunit C-terminal (50 μ were subjected to flow cytometric analysis using FITC-conjugated anti-IgG mAb. After centrifugation, platelets were subjected to flow cytometric analysis by using FITC-conjugated anti-IgG mAbs. Results are presented as histograms of cell numbers versus fluorescence intensity. This experiment was repeated at least three times and only a representative tracing was shown.

The contribution of specific amino acid involved in the inhibitory activity of CVX-α, and β☐C-terminal was explored. Sequence alignments between C-terminal homologues show that the region flanks with conserved residue are regions of sequence variability. These regions may confer the specificity for binding to GPVI. A site-directed mutagenesis technique was used to test the involvement of these key residues. The inhibitory effect of CVX-α, or β C-terminal on collagen-induced platelet aggregation was almost abolished by site 1 mutation (α subunit, W116A and β subunit, W108A), while not altered by site 2 mutantion (α subunit, F117A and β subunit, L109A) (FIG. 3A). Trowaglerix was used as a specific GPVI inducer to test the importance of these residues. The results were similar with collagen-treated group (FIG. 3B). Thus, the inhibitory effect of CVX-α, or β C-terminal is primarily mediated through GPVI, and the tryptophan residue is critical to its binding activity.

Example 4

Partial Sequencing of Trowaglerix and Activity of Fragments of Trowaglerix

Figure 4:
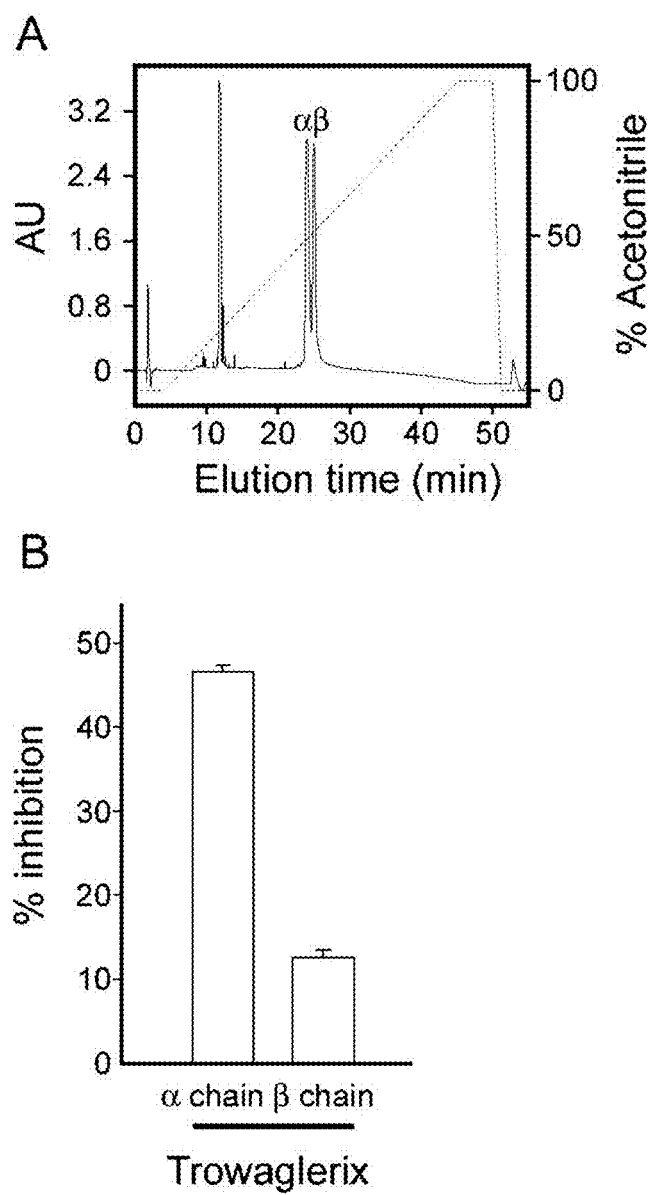

In light of the above results, it was suggested that the binding sites of snake venom CLPs toward their receptor are specific and probably located in C-terminal. In addition, the previous study demonstrated that trowaglerix, a high-mass heterodimeric multimer belonging to snake venom C-type lectins, specifically activates platelets via GPVI signal transduction, and induces the exposure of functional 0E1133 and platelet aggregation (Chang C H, Chung C H, Kuo H L, et al. *The highly specific platelet glycoprotein (GP) VI agonist trowaglerix impaired collagen-induced platelet aggregation ex vivo through matrix metalloproteinase-dependent GPVI shedding. J Thromb Haemost* 2008 April; 6(4):669-76). It was also found that α subunit of trowaglerix obtained from reverse-phase HPLC (FIG. 4A) exhibited significant inhibition toward collagen-induced platelet aggregation (FIG. 4B). To investigate whether small fragments of trowaglerix also exhibit inhibitory activity, trowaglerix was further fragmented by CNBr digestion. The fragments of trowaglerix also showed inhibition toward collagen-induced platelet aggregation (data not shown). Thus, the partial amino acid sequences of CNBr-cleaved fragments of α subunit of trowaglerix were determined by Edman degradation on an ABI model 477A protein sequencer (Applied Biosystems, Foster City, Calif., USA). These sequences are similar to several snake venom CLPs, but they still exhibit some distinctive difference (FIG. 5).

Example 5

Peptide Synthesis and Assay of Platelet Aggregation Inhibition

Snake venom CLPs have been widely used to study platelet receptors, and some of their crystal structures have been studied (Clemetson K J, Lu Q, Clemetson J M. *Snake C-type lectin-like proteins and platelet receptors. Pathophysiology of haemostasis and thrombosis* 2005; 34(4-5): 150-5; Batuwangala T, Leduc M, Gibbins J M, et al. *Structure of the snake-venom toxin convulxin. Acta custallographica* 2004 January; 60 (Pt 1):46-53). According to the putative binding sites of CLPs, several peptides of CLPs of C-terminus were synthesized (see Table 2). Some of them were tested to examine their effects on platelet functions. The results are shown in Table 1.

TABLE 1

Peptides synthesized on the basis of snake venom CLPs

| Peptides | Type | Sequence |
| --- | --- | --- |
| Tro-α10 | Synthesized | GFCKWMNVAC (SEQ ID NO: 25) |
| CVX-α6 (Convulxin) | Synthesized | RKWFVA (SEQ ID NO: 13) |
| Agg-α6 (Aggretin) | Synthesized | RKWVNY (SEQ ID NO: 14) |
| Agk-α6 (Agkistin) | Synthesized | RTWENV (SEQ ID NO: 21) |
| Tro-α6 (Trowaglerix) | Synthesized | CKWMNV (SEQ ID NO: 15) |
| CVX-β6 | Synthesized | NQWLSA (SEQ ID NO: 22) |
| Agg--β6 | Synthesized | TEWLNM (SEQ ID NO: 23) |
| Agk--β6 | Synthesized | NQWLSR (SEQ ID NO: 24) |
| Tro-α6 scramble | Synthesized | CWNKMV (SEQ ID NO: 16) |
| Tro-α6 W116A | Synthesized/Mutants | CKAMNV (SEQ ID NO: 17) |
| Tro-α6 M117A | Synthesized/Mutants | CKWANV (SEQ ID NO: 18) |
| Tro-α6 W116A/M117A | Synthesized/Mutants | CKAANV (SEQ ID NO: 19) |
| CVX-αF | Synthesized | RKWFV (SEQ ID NO: 10) |
| CVX-αB | Synthesized | KWFVA (SEQ ID NO: 9) |
| Agg-αF | Synthesized | RKWVN (SEQ ID NO: 11) |
| Agg-αB | Synthesized | KWVNY (SEQ ID NO: 8) |
| Tro-αF | Synthesized | CKWMN (SEQ ID NO: 12) |
| Tro-αB | Synthesized | KWMNV (SEQ ID NO: 7) |
| Tro-α cyclic12 | Synthesized | GFCKWMNVACAQ (SEQ ID NO: 30) |
| Tro-α cyclic10 | Synthesized | CKWMNVACAQ (SEQ ID NO: 27) |

TABLE 1-continued

Peptides synthesized on the basis of snake venom CLPs

| Peptides | Type | Sequence |
|---|---|---|
| Tro-α cyclic 8 | Synthesized | CKWMNVAC (SEQ ID NO: 26) |
| d-form Tro-α6 | Synthesized | C(dK)WM(dN)V (SEQ ID NO: 20) |
| Tro-α derivative | Synthesized | LFHVWDYYDR (SEQ ID NO: 28) |
| Tro-α derivative | Synthesized | LFHVWDYTDR (SEQ ID NO: 29) |

TABLE 2

Effects of synthetic peptides (at 100 μg/ml) derived from snake venom C-type lectins on platelet aggregation.

| Peptides | Type | Inhibition of the collagen-induced aggregation (%) |
|---|---|---|
| Tro-α10 | Synthesized | 93.75 ± 6.25 (IC50: 35.17 ± 11.00 ((30.42 ± 9.52 μM)) |
| CVX-α6 (Convulxin) | Synthesized | 28.66 ± 5.10 |
| Agg-α6 (Aggretin) | Synthesized | 21.67 ± 9.33 |
| Tro-α6 (Trowaglerix) | Synthesized | 44.30 ± 5.86 (IC50: 83.38 ± 8.65 μg/ml (106.90 ± 11.09 μM) |
| Agk--β6 | Synthesized | 24.55 ± 7.63 |
| Tro-α6 W116A | Synthesized/Mutants | 12.28 ± 2.40 |
| Tro-α6 M117A | Synthesized/Mutants | 52.91 ± 15.90 |
| d-form Tro-α6 | Synthesized | 89.44 ± 6.49 (IC50: 6.82 ± 3.34 μg/ml (8.75 ± 4.29 μM) |

As shown in Table 2, the platelet aggregation activity of the mutant Tro-α6 (W116A) wherein tryptophan at position 116 of Tro-α6 was substituted with alanine was decreased dramatically.

Example 6

Platelet Aggregation Studies

Figure 6:
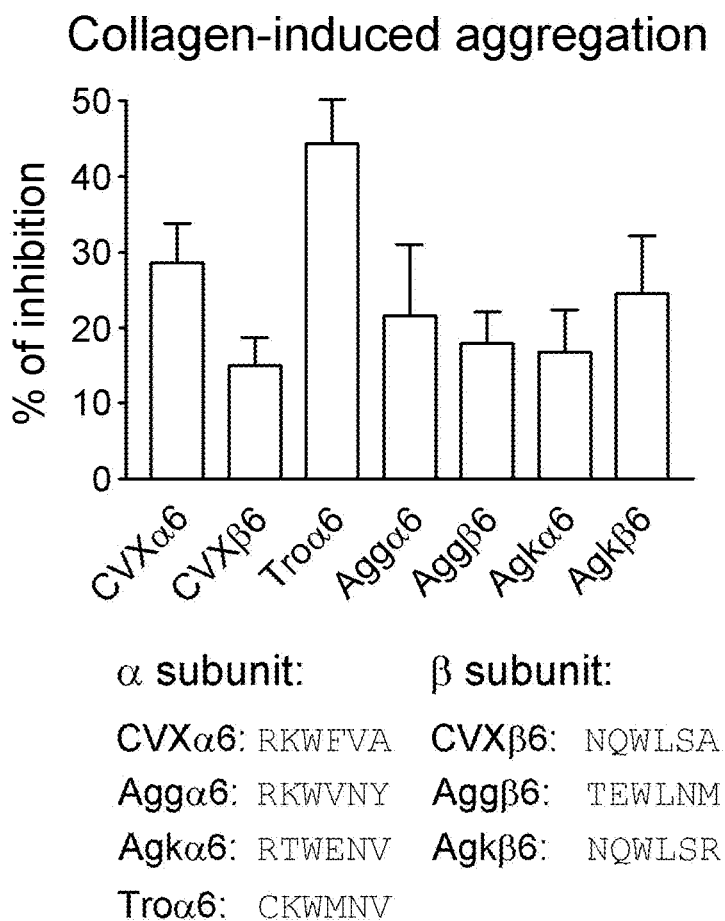
Figure 7:
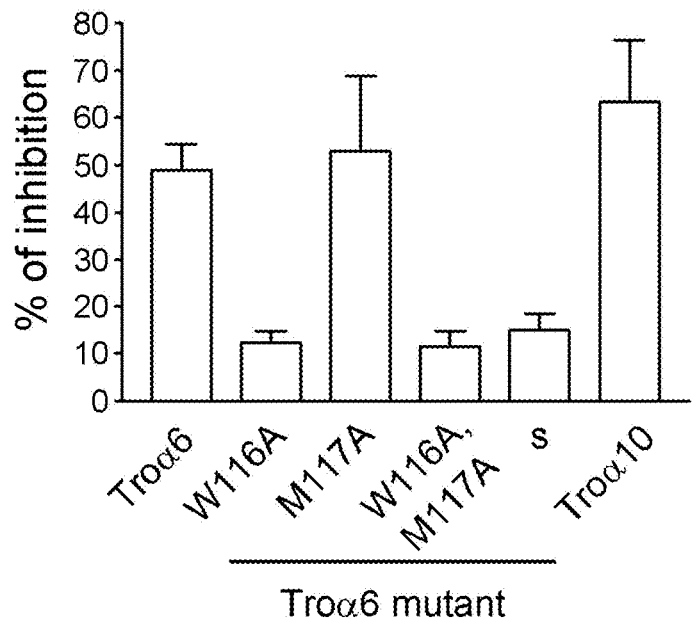

At first, several hexapeptides of CLPs, including trowaglerix, convulxin, aggretin, and agkistin were used to investigate their effects on collagen-induced platelet aggregation. As shown in FIG. 6, hexapeptide of trowaglerix α subunit (Troα6: 100 μg/ml, 128.2 μM) showed the most potent inhibitory effect (almost 50% inhibition) on collagen-induced aggregation while other hexapeptides exerted around 15-30% inhibition. Because of its greater inhibitory activity, this hexapeptide (CKWMNV) was chosen for further study. Therefore, amino acid mutation of hexapeptide was used to demonstrate which amino acid is critical for its inhibitory activity. The inhibitory activity of hexpeptide was diminished by the mutation of the specific amino acid residue (W116A) (FIG. 7A), indicating that the amino acid of hexapeptide (Tryptophan) is critical for the expression of its inhibitory activity. Extended synthetic peptide (Troα10, GFCKWMNVAC) also exhibited 60% inhibition on collagen-induced aggregation. However, scrambled peptide of trowaglerix α subunit (s) showed little effect. Other modified decapeptides (S1, S2 or S1+2) were also used to investigate their effects on collagen-induced platelet aggregation. FIG. 7B shows effects of Troα10 and modified decapeptides (100 μg/ml) derived from trowaglerix α on collagen-induced aggregation. Washed platelets were preincubated with decapeptide (α10), hexapeptide (α6), d-form hexapeptide (d-α6), modified decapeptides (S1, S2 or S1+2) at 37° C. for 3 min, and then collagen was added to trigger platelet aggregation. Results are expressed as percentage of inhibition. Data are presented as mean+SEM (n>3).

Figure 8:
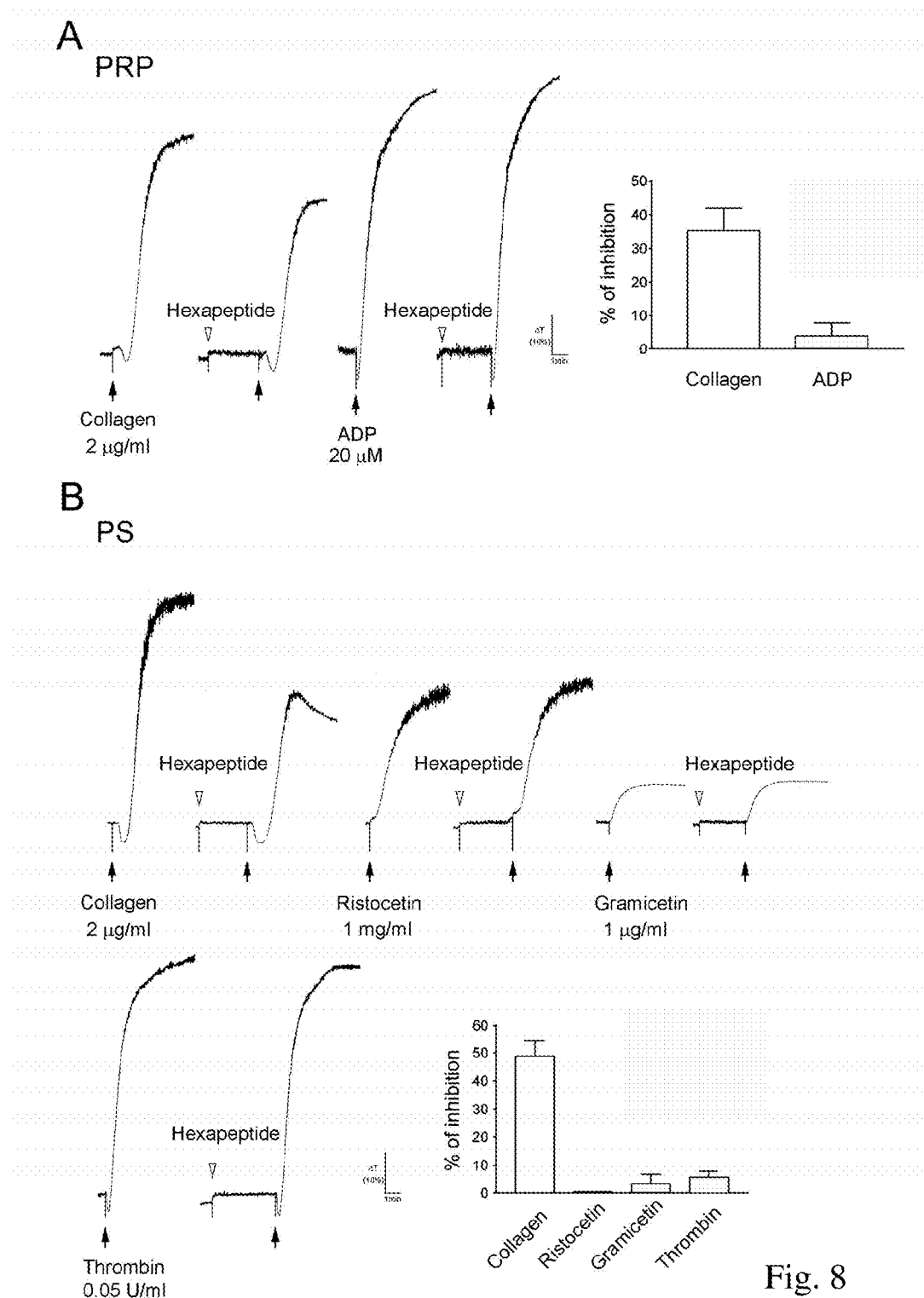

Other platelet agonists were also used to evaluate whether the inhibition of hexapeptide is specific. As shown in FIG. 8, Troα6 specifically inhibited collagen-induced platelet aggregation whereas it did not have good effect on the platelet aggregation stimulated by ADP or thrombin. In addition, this hexapeptide provide less effect on platelet agglutination caused by ristocetin or gramicetin (a GPIb agonist). In human platelet-rich plasma (PRP), this hexapeptide also exhibited similar inhibition at 200 μg/ml (256.4 μM). Therefore, it is suggested that Troα6 may interact with collagen receptor (α2β1 or GPVI), leading to inhibition of platelet aggregation.

Table 3 shows the effect of hexapeptide (Troα6) and decapeptide (Troα10) on collagen-induced platelet aggregation ex vivo. The aggregation response of platelet-rich plasma (PRP) prepared from mice treated with PBS (CTL), hexapeptide (30 mg/kg) or decapeptide (10 mg/kg) was initiated by the addition of collagen (3 μg/ml). Results are expressed as percentage of inhibition.

| | % of inhibition |
|---|---|
| Hexapeptide 30 mg/kg | 46.76 ± 4.37 (n = 11) |
| Decapeptide 10 mg/kg | 55.87 ± 10.82 (n = 11) |

Example 7

Figure 9:
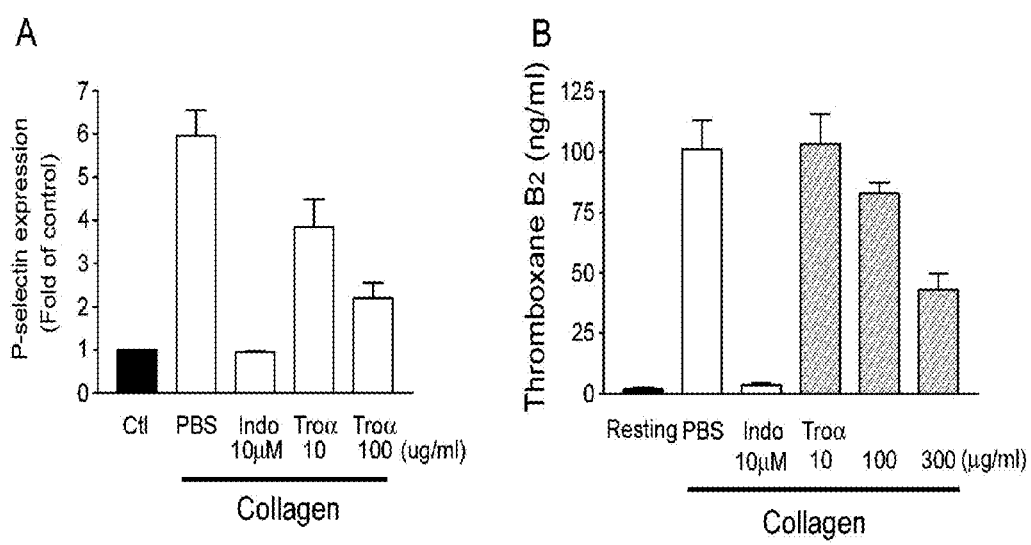

Inhibitory Effect of Hexapeptide on P-Selectin Expression and Thromboxane $B_2$ Formation P-selectin, stored in α-granules of platelets, is a marker of platelet activation. Troα6 concentration-dependently inhibited P-selectin expression of platelets caused by collagen (FIG. 9A).

Thromboxane $A_2$ formation is a landmark of platelet activation and its stable metabolite, thromboxane $B_2$, was used as an index for measuring thromboxane $A_2$ formation. The level of thromboxane $B_2$ formation of washed human platelets in response to collagen was 101.00±11.99 ng/ml. Troα6 concentration-dependently inhibited thromboxane $B_2$ formation caused by collagen (15.93±5.81% inhibition at 128.2 μM, 55.23±12.42% inhibition at 684.6 μM) (FIG. 9B).

Example 8

Hexapeptide/Decapeptide Binds to Platelet GPVI

Figure 10:
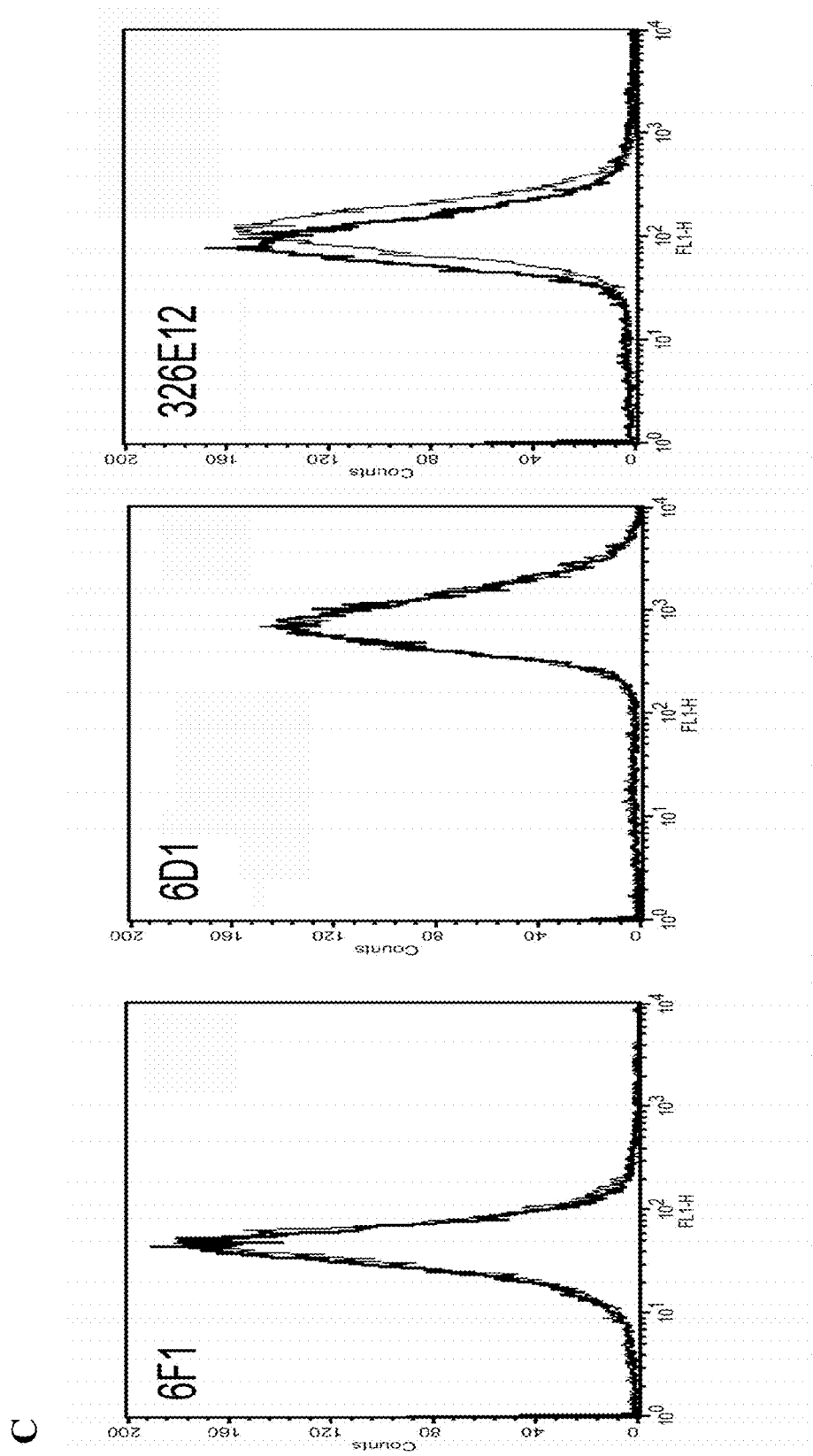

The binding of FITC-hexapeptide to washed platelets was analyzed by flow cytometry and non-specific binding was performed using FITC-BSA as a probe. As shown in FIG. 10A, FITC-hexapeptide concentration-dependently bound to platelets and almost saturated at a concentration of 100 μg/ml (128.2 μM). Therefore, the effect of Troα6 on the binding of membrane GPIa/IIa, GPIb and GPVI was investigated. Platelets treated with PBS or Troα6 (100 μg/ml) were probed by anti-αIIbβ3 mAb (7E3), anti-GPIb mAb (AP1), anti-α2β1 integrin mAb (MAB1998) and anti-GPVI mAb (6B12), respectively, and their bindings were expressed by the histograms of cell numbers versus fluorescence intensity. Hexapeptide Troα6 significantly inhibited the binding of GPVI mAb (6B12) to platelets. In contrast, hexapeptide treatment showed less effect on anti-αIIbβ3 mAb (7E3), anti-α2β1 integrin (MAB1998) or anti-GPIb (AP1) binding to platelets (FIG. 10B).

Effect of decapeptide on the expression of membrane GPIa/IIa, GPIb and GPVI in human platelets. Washed platelets were preincubated with PBS (thin line) or decapeptide (thick line, 300 µg/ml), and probed by anti-GPIa/IIa (6F1), anti-GPIb (6D1) or anti-GPVI (326E12) mAbs. After centrifugation, platelets were subjected to flow cytometric analysis using FITC-conjugated anti-IgG mAb (FIG. 10C). In flow cytometric analysis, we found that hexapeptide/decapeptide specifically inhibited anti-GPVI mAb binding, but not anti-α2β1 integrin mAb binding (FIG. 10B-C). Therefore, we propose that hexapeptide/decapeptide inhibits collagen-induced aggregation via interacting with collagen receptor, GPVI Example 9

Antithrombotic Activity of Hexapeptide/Deca in Ex Vivo and In Vivo Model

Whether Troα6 also exerted antithrombotic effect in vivo was next investigated. First, the responsiveness of PRP prepared from Troα6-treated mice toward collagen was examined. The platelet aggregation response induced by collagen was significantly inhibited (FIG. 11A, % of inhibition: 46.76±4.73, n=11) in PRP prepared from mice pretreated with hexapeptide (30 mg/kg) for 5 min. However, the platelet count, as measured at 5 min after the administration of hexapeptide, was not altered (11.18±0.30 vs 11.41±0.19× $10^8$/ml for control).

Furthermore, the antithrombotic effect of Troα6 in vivo was examined. Thrombus formation was observed in irradiated mesenteric venules of mice pretreated with fluorescein sodium. IV administration of Troα6 (30 mg/kg) delayed platelet-rich thrombus formation and significantly prolonged the occlusion time from 111.1±5.1 s (control, n=17) to 315.9±21.9 s (n=20). On the other hand, at the dose of 250 mg/kg, aspirin also increased the occlusion time to 298.7±29.6 s (n=15, Table 4). These data showed that intravenous administration of hexapeptide exhibited antithrombic activity both in vivo and ex vivo in mice.

TABLE 4

Effect of hexapeptide (Troα6) on fluorescent dye-induced platelet-rich thrombus formation in the irradiated mesenteric venules of mice

|  | Occlusion time (s) | n |
|---|---|---|
| Control (PBS) | 111.1 ± 5.1 | 17 |
| Hexapeptide, 30 mg/kg | 315.9 ± 21.9 *** | 20 |
| Aspirin, 250 mg/kg | 298.7 ± 29.6 *** | 15 |

Values are presented as means ± S.E.M of experimental number (n) indicated.
*** $p < 0.001$ compared with control.

The degree of delaying occlusion time of this hexapeptide is similar to those of aspirin (250 mg/kg), however, the dose of hexapeptide used is lower than aspirin (Table 4). Furthermore, hexapeptide did not significantly prolong bleeding time, indicating that hexapeptide may preferentially inhibit thrombus formation with little effect on bleeding time. Up to date, there are few GPVI inhibitors reported except anti-GPVI antibodies. In this study, we first reveal the GPVI-targeting synthetic peptide of trowaglerix α subunit, providing a novel skeleton for developing the specific small-molecule antagonist of platelet GPVI for prevention of arterial thrombosis. The optimization of these peptides with the aid of computer modeling is in progress.

In addition, Troα10 (10 mg/kg) also markedly prolonged the occlusion time from 153.0±13.5 s (control, n=13) to 294.5±25.4 s (n=19) (Table 5). On the other hand, at the dose of 250 mg/kg, aspirin also increased the occlusion time to 298.7±29.6 s (n=15). These data showed that intravenous administration of hexapeptide or decapeptide exhibited antithrombic activity both in vivo and ex vivo in mice.

TABLE 2

Effect of decapeptide (Troα10) on fluorescent dye-induced platelet-rich thrombus formation in the irradiated mesenteric venules of mice

|  | Occlusion time (s) | n |
|---|---|---|
| Control (PBS) | 153.0 ± 13.5 | 13 |
| Decapeptide, 10 mg/kg | 294.5 ± 25.4 *** | 19 |

In addition, bleeding represented as the common unwanted effect after antithrombotic therapy. The tail transection model was used to examine the influence of hexapeptide on hemostasis in vivo. As shown in FIG. 11B, hexapeptide (30 mg/kg) did not apparently affect the bleeding time in mice (3.50±0.79 min vs control 1.90+0.28 min, p>0.05) comparable to tirofiban (0.4 mg/kg, a commercial GPIIb/IIIa antagonist, 4.20±1.20 min). In contrast, aspirin at the dose of 250 mg/kg, significantly prolonged the bleeding time (8.20±0.91 min, p<0.001).

Example 10

Effect of Decapeptide on Cytosolic Ca2+ Mobilization Caused by Collagen

Using the specific $Ca^{2+}$ probe Fura-2/AM, we examined the effect of decapeptide on $[Ca^{2+}]i$ elevation in platelets stimulated with collagen. We found that collagen-evoked increase of $[Ca^{2+}]i$ was inhibited by decapeptide in a concentration-dependent manner (FIG. 12).

SEQUENCE LISTING

<160> NUMBER OF SEQ ID NOS: 47

<210> SEQ ID NO 1
<211> LENGTH: 135
<212> TYPE: PRT
<213> ORGANISM: Artificial sequence
<220> FEATURE:
<223> OTHER INFORMATION: Convulxin

```
<400> SEQUENCE: 1

Gly Leu His Cys Pro Ser Asp Trp Tyr Tyr Tyr Asp Gln His Cys Tyr
1               5                   10                  15

Arg Ile Phe Asn Glu Glu Met Asn Trp Glu Asp Ala Glu Trp Phe Cys
                20                  25                  30

Thr Lys Gln Ala Lys Gly Ala His Leu Val Ser Ile Lys Ser Ala Lys
            35                  40                  45

Glu Ala Asp Phe Val Ala Trp Met Val Thr Gln Asn Ile Glu Glu Ser
        50                  55                  60

Phe Ser His Val Ser Ile Gly Leu Arg Val Gln Asn Lys Glu Lys Gln
65                  70                  75                  80

Cys Ser Thr Lys Trp Ser Asp Gly Ser Ser Val Ser Tyr Asp Asn Leu
                85                  90                  95

Leu Asp Leu Tyr Ile Thr Lys Cys Ser Leu Leu Lys Lys Glu Thr Gly
                100                 105                 110

Phe Arg Lys Trp Phe Val Ala Ser Cys Ile Gly Lys Ile Pro Phe Val
            115                 120                 125

Cys Lys Phe Pro Pro Gln Cys
            130                 135

<210> SEQ ID NO 2
<211> LENGTH: 136
<212> TYPE: PRT
<213> ORGANISM: Artificial sequence
<220> FEATURE:
<223> OTHER INFORMATION: Aggretin

<400> SEQUENCE: 2

Gly Leu Glu Asp Cys Asp Phe Gly Trp Ser Pro Tyr Asp Gln His Cys
1               5                   10                  15

Tyr Gln Ala Phe Asn Glu Gln Lys Thr Trp Asp Glu Ala Glu Lys Phe
                20                  25                  30

Cys Arg Ala Gln Glu Asn Gly Ala His Leu Ala Ser Ile Glu Ser Asn
            35                  40                  45

Gly Glu Ala Asp Phe Val Ser Trp Leu Ile Ser Gln Lys Asp Glu Leu
        50                  55                  60

Ala Asp Glu Asp Tyr Val Trp Ile Gly Leu Arg Ala Gln Asn Lys Glu
65                  70                  75                  80

Gln Gln Cys Ser Ser Glu Trp Ser Asp Gly Ser Ser Val Ser Tyr Glu
                85                  90                  95

Asn Leu Ile Asp Leu His Thr Lys Lys Cys Gly Ala Leu Glu Lys Leu
                100                 105                 110

Thr Gly Phe Arg Lys Trp Val Asn Tyr Cys Glu Gln Met His Ala
            115                 120                 125

Phe Val Cys Lys Leu Leu Pro Tyr
            130                 135

<210> SEQ ID NO 3
<211> LENGTH: 132
<212> TYPE: PRT
<213> ORGANISM: Artificial sequence
<220> FEATURE:
<223> OTHER INFORMATION: Agkistin

<400> SEQUENCE: 3

Asp Cys Leu Pro Gly Trp Ser Ser Tyr Ile Arg Phe Cys Tyr Gln Pro
1               5                   10                  15
```

```
Phe Lys Leu Leu Lys Thr Trp Glu Asp Ala Glu Arg Phe Cys Thr Glu
            20                  25                  30

Gln Ala Asn Gly Gly His Leu Val Ser Phe Glu Ser Ala Arg Glu Ala
        35                  40                  45

Asp Phe Val Ala Gly Val Leu Ser Glu Asn Ile Lys Ile Lys Pro Tyr
50                  55                  60

Val Trp Ile Gly Leu Arg Val Gln Asn Glu Gly Gln Gln Cys Ser Ser
65                  70                  75                  80

Lys Trp Ser Asp Ser Ser Lys Val Ser Tyr Glu Asn Leu Val Glu Pro
                85                  90                  95

Phe Ser Lys Cys Phe Val Leu Lys Lys Asp Thr Gly Phe Arg Thr
            100                 105                 110

Trp Glu Asn Val Tyr Cys Gly Leu Lys His Val Phe Met Cys Lys Tyr
                115                 120                 125

Leu Lys Pro Arg
        130

<210> SEQ ID NO 4
<211> LENGTH: 99
<212> TYPE: PRT
<213> ORGANISM: Artificial sequence
<220> FEATURE:
<223> OTHER INFORMATION: Trowaglerix

<400> SEQUENCE: 4

Asp Phe Lys Cys Pro Ser Glu Trp Tyr Ala Tyr Asp Gln His Cys Tyr
1               5                   10                  15

Arg Ile Ile Asn Lys Pro Gln Thr Trp Ala Asp Ala Glu Lys Phe Pro
            20                  25                  30

Lys Gln Ala Lys Gly Gly Val Thr Gln Asn Ile Glu Thr Pro Phe His
        35                  40                  45

Tyr Val Trp Ile Gly Leu Arg Val Gln Asn Lys Lys Gln Cys Ser
50                  55                  60

Asn Lys Pro Gly Ala Leu His Gln His Lys Gly Phe Cys Lys Trp Met
65                  70                  75                  80

Asn Val Ala Cys Ala Gln Lys His Pro Phe Val Cys Lys Phe Pro Pro
                85                  90                  95

Gln Cys Ala

<210> SEQ ID NO 5
<211> LENGTH: 135
<212> TYPE: PRT
<213> ORGANISM: Artificial sequence
<220> FEATURE:
<223> OTHER INFORMATION: Agglucetin

<400> SEQUENCE: 5

Asp Phe Asn Cys Pro Pro Gly Trp Ser Ala Tyr Asp Gln Tyr Cys Tyr
1               5                   10                  15

Gln Val Ile Lys Glu Pro Lys Asn Trp Asp Asp Ala Glu Arg Phe Cys
            20                  25                  30

Thr Glu Gln Ala Asp Gly Gly His Leu Val Ser Ile Glu Ser Lys Gly
        35                  40                  45

Glu Arg Asp Phe Val Ala Gln Leu Val Ser Gln Asn Ile Glu Ser Val
    50                  55                  60

Glu Asp His Val Trp Thr Gly Leu Arg Val Gln Asn Lys Glu Lys Gln
65                  70                  75                  80
```

```
Cys Ser Thr Glu Trp Ser Asp Gly Ser Ser Val Ser Tyr Glu Asn Leu
                85                  90                  95

Leu Glu Leu Tyr Met Arg Lys Cys Gly Ala Leu Glu Arg Glu Thr Gly
            100                 105                 110

Phe His Lys Trp Ile Asn Leu Gly Cys Ile Gln Leu Asn Pro Phe Val
        115                 120                 125

Cys Lys Phe Pro Pro Gln Cys
    130             135

<210> SEQ ID NO 6
<211> LENGTH: 125
<212> TYPE: PRT
<213> ORGANISM: Artificial sequence
<220> FEATURE:
<223> OTHER INFORMATION: Convulxin Beta-subunit of the CLPs

<400> SEQUENCE: 6

Gly Phe Cys Cys Pro Ser His Trp Ser Ser Tyr Asp Arg Tyr Cys Tyr
1               5                   10                  15

Lys Val Phe Lys Gln Glu Met Thr Trp Ala Asp Ala Glu Lys Phe Cys
            20                  25                  30

Thr G

```
<223> OTHER INFORMATION: CVX-alpha B

<400> SEQUENCE: 9

Lys Trp Phe Val Ala
1               5

<210> SEQ ID NO 10
<211> LENGTH: 5
<212> TYPE: PRT
<213> ORGANISM: Artificial sequence
<220> FEATURE:
<223> OTHER INFORMATION: CVX-alpha F

<400> SEQUENCE: 10

Arg Lys Trp Phe Val
1               5

<210> SEQ ID NO 11
<211> LENGTH: 5
<212> TYPE: PRT
<213> ORGANISM: Artificial sequence
<220> FEATURE:
<223> OTHER INFORMATION: Agg-alpha F

<400> SEQUENCE: 11

Arg Lys Trp Val Asn
1               5

<210> SEQ ID NO 12
<211> LENGTH: 5
<212> TYPE: PRT
<213> ORGANISM: Artificial sequence
<220> FEATURE:
<223> OTHER INFORMATION: Tro-alpha F

<400> SEQUENCE: 12

Cys Lys Trp Met Asn
1               5

<210> SEQ ID NO 13
<211> LENGTH: 6
<212> TYPE: PRT
<213> ORGANISM: Artificial sequence
<220> FEATURE:
<223> OTHER INFORMATION: CVX-alpha 6(Convulxin)

<400> SEQUENCE: 13

Arg Lys Trp Phe Val Ala
1               5

<210> SEQ ID NO 14
<211> LENGTH: 6
<212> TYPE: PRT
<213> ORGANISM: Artificial sequence
<220> FEATURE:
<223> OTHER INFORMATION: Agg-alpha 6(Aggretin)

<400> SEQUENCE: 14

Arg Lys Trp Val Asn Tyr
1               5

<210> SEQ ID NO 15
<211> LENGTH: 6
<212> TYPE: PRT
<213> ORGANISM: Artificial sequence
<220> FEATURE:
<223> OTHER INFORMATION: Tro-alpha 6(Trowaglerix)
```

```
<400> SEQUENCE: 15

Cys Lys Trp Met Asn Val
1               5

<210> SEQ ID NO 16
<211> LENGTH: 6
<212> TYPE: PRT
<213> ORGANISM: Artificial sequence
<220> FEATURE:
<223> OTHER INFORMATION: Tro-alpha 6 scramble

<400> SEQUENCE: 16

Cys Trp Asn Lys Met Val
1               5

<210> SEQ ID NO 17
<211> LENGTH: 6
<212> TYPE: PRT
<213> ORGANISM: Artificial sequence
<220> FEATURE:
<223> OTHER INFORMATION: Tro-alpha 6 W116A

<400> SEQUENCE: 17

Cys Lys Ala Met Asn Val
1               5

<210> SEQ ID NO 18
<211> LENGTH: 6
<212> TYPE: PRT
<213> ORGANISM: Artificial sequence
<220> FEATURE:
<223> OTHER INFORMATION: Tro-alpha 6 M117A

<400> SEQUENCE: 18

Cys Lys Trp Ala Asn Val
1               5

<210> SEQ ID NO 19
<211> LENGTH: 6
<212> TYPE: PRT
<213> ORGANISM: Artificial sequence
<220> FEATURE:
<223> OTHER INFORMATION: Tro-alpha 6 W116A/M117A

<400> SEQUENCE: 19

Cys Lys Ala Ala Asn Val
1               5

<210> SEQ ID NO 20
<211> LENGTH: 6
<212> TYPE: PRT
<213> ORGANISM: Artificial sequence
<220> FEATURE:
<223> OTHER INFORMATION: d-form Tro-alpha 6

<400> SEQUENCE: 20

Cys Lys Trp Met Asn Val
1               5

<210> SEQ ID NO 21
<211> LENGTH: 6
<212> TYPE: PRT
<213> ORGANISM: Artificial sequence
<220> FEATURE:
<223> OTHER INFORMATION: Agk-alpha 6(Agkistin)
```

```
<400> SEQUENCE: 21

Arg Thr Trp Glu Asn Val
1               5

<210> SEQ ID NO 22
<211> LENGTH: 6
<212> TYPE: PRT
<213> ORGANISM: Artificial sequence
<220> FEATURE:
<223> OTHER INFORMATION: CVX-beta 6

<400> SEQUENCE: 22

Asn Gln Trp Leu Ser Ala
1               5

<210> SEQ ID NO 23
<211> LENGTH: 6
<212> TYPE: PRT
<213> ORGANISM: Artificial sequence
<220> FEATURE:
<223> OTHER INFORMATION: Agg--beta 6

<400> SEQUENCE: 23

Thr Glu Trp Leu Asn Met
1               5

<210> SEQ ID NO 24
<211> LENGTH: 6
<212> TYPE: PRT
<213> ORGANISM: Artificial sequence
<220> FEATURE:
<223> OTHER INFORMATION: Agk--beta 6

<400> SEQUENCE: 24

Asn Gln Trp Leu Ser Arg
1               5

<210> SEQ ID NO 25
<211> LENGTH: 10
<212> TYPE: PRT
<213> ORGANISM: Artificial sequence
<220> FEATURE:
<223> OTHER INFORMATION: Tro-alpha 10

<400> SEQUENCE: 25

Gly Phe Cys Lys Trp Met Asn Val Ala Cys
1               5                   10

<210> SEQ ID NO 26
<211> LENGTH: 8
<212> TYPE: PRT
<213> ORGANISM: Artificial sequence
<220> FEATURE:
<223> OTHER INFORMATION: Tro-alpha cyclic 8

<400> SEQUENCE: 26

Cys Lys Trp Met Asn Val Ala Cys
1               5

<210> SEQ ID NO 27
<211> LENGTH: 10
<212> TYPE: PRT
<213> ORGANISM: Artificial sequence
<220> FEATURE:
<223> OTHER INFORMATION: Tro-alpha cyclic10

<400> SEQUENCE: 27
```

```
Cys Lys Trp Met Asn Val Ala Cys Ala Gln
1               5                   10

<210> SEQ ID NO 28
<211> LENGTH: 10
<212> TYPE: PRT
<213> ORGANISM: Artificial sequence
<220> FEATURE:
<223> OTHER INFORMATION: Tro-alpha derivative

<400> SEQUENCE: 28

Leu Phe His Val Trp Asp Tyr Tyr Asp Arg
1               5                   10

<210> SEQ ID NO 29
<211> LENGTH: 10
<212> TYPE: PRT
<213> ORGANISM: Artificial sequence
<220> FEATURE:
<223> OTHER INFORMATION: Tro-alpha derivative

<400> SEQUENCE: 29

Leu Phe His Val Trp Asp Tyr Thr Asp Arg
1               5                   10

<210> SEQ ID NO 30
<211> LENGTH: 12
<212> TYPE: PRT
<213> ORGANISM: Artificial sequence
<220> FEATURE:
<223> OTHER INFORMATION: Tro-alpha cyclic12

<400> SEQUENCE: 30

Gly Phe Cys Lys Trp Met Asn Val Ala Cys Ala Gln
1               5                   10

<210> SEQ ID NO 31
<211> LENGTH: 32
<212> TYPE: PRT
<213> ORGANISM: Artificial sequence
<220> FEATURE:
<223> OTHER INFORMATION: Recombinant  CVX alpha C-terminal104-135

<400> SEQUENCE: 31

Cys Ser Leu Leu Lys Lys Glu Thr Gly Phe Arg Lys Trp Phe Val Ala
1               5                   10                  15

Ser Cys Ile Gly Lys Ile Pro Phe Val Cys Lys Phe Pro Pro Gln Cys
            20                  25                  30

<210> SEQ ID NO 32
<211> LENGTH: 32
<212> TYPE: PRT
<213> ORGANISM: Artificial sequence
<220> FEATURE:
<223> OTHER INFORMATION: Recombinant CVX beta C-terminal94-125

<400> SEQUENCE: 32

Glu Glu Phe Glu Cys Leu Ile Ser Arg Thr Phe Asp Asn Gln Trp Leu
1               5                   10                  15

Ser Ala Pro Cys Ser Asp Thr Tyr Ser Phe Val Cys Lys Phe Glu Ala
            20                  25                  30

<210> SEQ ID NO 33
<211> LENGTH: 5
<212> TYPE: PRT
```

```
<213> ORGANISM: Artificial sequence
<220> FEATURE:
<223> OTHER INFORMATION: Peptide
<220> FEATURE:
<221> NAME/KEY: X2
<222> LOCATION: (1)..(1)
<223> OTHER INFORMATION: X is selected from the group consisting of: Lys
      (K), dLys (dK), Arg (R), Gly (G), Ala (A), Val (V), Leu (L), Ile
      (I), Ser (S), Thr (T), Cys (C), Gln (Q), Asn (N), Glu (E) and Asp
      (D).
<220> FEATURE:
<221> NAME/KEY: X3
<222> LOCATION: (3)..(3)
<223> OTHER INFORMATION: X3 is selected from the group consisting of:
      Phe (F), Tyr (Y), Trp (W), Gly (G), Ala (A), Val (V), Leu (L), Ile
      (I), Ser (S), Thr (T), Cys (C), Met (M), Asn (N), Gln (Q), Glu (E)
      and Asp (D).
<220> FEATURE:
<221> NAME/KEY: X4
<222> LOCATION: (4)..(4)
<223> OTHER INFORMATION: X4 is selected from the group consisting of:
      Gly (G), Ala (A), Val (V), Leu (L), Ile (I), Ser (S), Thr (T), Cys
      (C), Gln (Q) and Asn (N).
<220> FEATURE:
<221> NAME/KEY: X5
<222> LOCATION: (5)..(5)
<223> OTHER INFORMATION: X5 is selected from the group consisting of:
      Gly (G), Ala (A), Val (V), Leu (L), Ile (I), Ser (S), Thr (T), Cys
      (C), Phe (F), Tyr (Y), Trp (W), Met (M), Lys (K) and Arg (R).

<400> SEQUENCE: 33

Xaa Trp Xaa Xaa Xaa
1               5

<210> SEQ ID NO 34
<211> LENGTH: 6
<212> TYPE: PRT
<213> ORGANISM: Artificial sequence
<220> FEATURE:
<223> OTHER INFORMATION: Peptide
<220> FEATURE:
<221> NAME/KEY: X1
<222> LOCATION: (1)..(1)
<223> OTHER INFORMATION: X1 is selected from the group consisting of:
      Arg (R), Lys (K), Gly (G), Ala (A), Val (V), Leu (L), Ile (I), Ser
      (S), Thr (T), Cys (C), Asn (N) and Gln (Q).
<220> FEATURE:
<221> NAME/KEY: X2
<222> LOCATION: (2)..(2)
<223> OTHER INFORMATION: X2 is selected from the group consisting of:
      Lys (K), dLys (dK), Arg (R), Gly (G), Ala (A), Val (V), Leu (L),
      Ile (I), Ser (S), Thr (T), Cys (C), Gln (Q), Asn (N), Glu (E) and
      Asp (D).
<220> FEATURE:
<221> NAME/KEY: X3
<222> LOCATION: (4)..(4)
<223> OTHER INFORMATION: X3 is selected from the group consisting of:
      Phe (F), Tyr (Y), Trp (W), Gly (G), Ala (A), Val (V), Leu (L), Ile
      (I), Ser (S), Thr (T), Cys (C), Met (M), Asn (N), Gln (Q), Glu (E)
      and Asp (D).
<220> FEATURE:
<221> NAME/KEY: X4
<222> LOCATION: (5)..(5)
<223> OTHER INFORMATION: X4 is selected from the group consisting of:
      Gly (G), Ala (A), Val (V), Leu (L), Ile (I), Ser (S), Thr (T), Cys
      (C), Gln (Q) and Asn (N).
<220> FEATURE:
<221> NAME/KEY: X5
<222> LOCATION: (6)..(6)
<223> OTHER INFORMATION: X5 is selected from the group consisting of:
      Gly (G), Ala (A), Val (V), Leu (L), Ile (I), Ser (S), Thr (T), Cys
      (C), Phe (F), Tyr (Y), Trp (W), Met (M), Lys (K) and Arg (R).

<400> SEQUENCE: 34

Xaa Xaa Trp Xaa Xaa Xaa
1               5
```

```
<210> SEQ ID NO 35
<211> LENGTH: 5
<212> TYPE: PRT
<213> ORGANISM: Artificial sequence
<220> FEATURE:
<223> OTHER INFORMATION: Peptide
<220> FEATURE:
<221> NAME/KEY: X1
<222> LOCATION: (1)..(1)
<223> OTHER INFORMATION: X1 is selected from the group consisting of:
      Arg (R), Lys (K), Gly (G), Ala (A), Val (V), Leu (L), Ile (I), Ser
      (S), Thr (T), Cys (C), Asn (N) and Gln (Q).
<220> FEATURE:
<221> NAME/KEY: X2
<222> LOCATION: (2)..(2)
<223> OTHER INFORMATION: X2 is selected from the group consisting of:
      Lys (K), dLys (dK), Arg (R), Gly (G), Ala (A), Val (V), Leu (L),
      Ile (I), Ser (S), Thr (T), Cys (C), Gln (Q), Asn (N), Glu (E) and
      Asp (D).
<220> FEATURE:
<221> NAME/KEY: X3
<222> LOCATION: (4)..(4)
<223> OTHER INFORMATION: X3 is selected from the group consisting of:
      Phe (F), Tyr (Y), Trp (W), Gly (G), Ala (A), Val (V), Leu (L), Ile
      (I), Ser (S), Thr (T), Cys (C), Met (M), Asn (N), Gln (Q), Glu (E)
      and Asp (D).
<220> FEATURE:
<221> NAME/KEY: X4
<222> LOCATION: (5)..(5)
<223> OTHER INFORMATION: X4 is selected from the group consisting of:
      Gly (G), Ala (A), Val (V), Leu (L), Ile (I), Ser (S), Thr (T), Cys
      (C), Gln (Q) and Asn (N).

<400> SEQUENCE: 35

Xaa Xaa Trp Xaa Xaa
1               5

<210> SEQ ID NO 36
<211> LENGTH: 5
<212> TYPE: PRT
<213> ORGANISM: Artificial sequence
<220> FEATURE:
<223> OTHER INFORMATION: Peptide
<220> FEATURE:
<221> NAME/KEY: X2
<222> LOCATION: (1)..(1)
<223> OTHER INFORMATION: X2 is selected from the group consisting of:
      Lys (K), dLys (dK), Arg (R), Gly (G), Ala (A), Val (V), Leu (L),
      Ile (I), Ser (S), Thr (T), Cys (C), Gln (Q), Asn (N), Glu (E) and
      Asp (D).
<220> FEATURE:
<221> NAME/KEY: X3
<222> LOCATION: (3)..(3)
<223> OTHER INFORMATION: X3 is selected from the group consisting of:
      Phe (F), Tyr (Y), Trp (W), Gly (G), Ala (A), Val (V), Leu (L), Ile
      (I), Ser (S), Thr (T), Cys (C), Met (M), Asn (N), Gln (Q), Glu (E)
      and Asp (D).
<220> FEATURE:
<221> NAME/KEY: X4
<222> LOCATION: (4)..(4)
<223> OTHER INFORMATION: X4 is selected from the group consisting of:
      Tyr (Y), Gly (G), Ala (A), Val (V), Leu (L), Ile (I), Ser (S), Thr
      (T), Cys (C), Gln (Q) and Asn (N).
<220> FEATURE:
<221> NAME/KEY: X5
<222> LOCATION: (5)..(5)
<223> OTHER INFORMATION: X5 is selected from the group consisting of:
      Gly (G), Ala (A), Val (V), Leu (L), Ile (I), Ser (S), Thr (T), Cys
      (C), Phe (F), Tyr (Y), Trp (W), Met (M), Lys (K) and Arg (R).

<400> SEQUENCE: 36

Xaa Trp Xaa Xaa Xaa
1               5
```

```
<210> SEQ ID NO 37
<211> LENGTH: 5
<212> TYPE: PRT
<213> ORGANISM: Artificial sequence
<220> FEATURE:
<223> OTHER INFORMATION: Peptide
<220> FEATURE:
<221> NAME/KEY: X1
<222> LOCATION: (1)..(1)
<223> OTHER INFORMATION: X1 is selected from the group consisting of:
      Arg (R), Lys (K), Gly (G), Ala (A), Val (V), Leu (L), Ile (I), Ser
      (S), Thr (T), Cys (C), Asn (N) and Gln (Q).
<220> FEATURE:
<221> NAME/KEY: X2
<222> LOCATION: (2)..(2)
<223> OTHER INFORMATION: X2 is selected from the group consisting of:
      Lys (K), dLys (dK), Arg (R), Gly (G), Ala (A), Val (V), Leu (L),
      Ile (I), Ser (S), Thr (T), Cys (C), Gln (Q), Asn (N), Glu (E) and
      Asp (D).
<220> FEATURE:
<221> NAME/KEY: X3
<222> LOCATION: (4)..(4)
<223> OTHER INFORMATION: X3 is selected from the group consisting of:
      Phe (F), Tyr (Y), Trp (W), Gly (G), Ala (A), Val (V), Leu (L), Ile
      (I), Ser (S), Thr (T), Cys (C), Met (M), Asn (N), Gln (Q), Glu (E)
      and Asp (D).
<220> FEATURE:
<221> NAME/KEY: X4
<222> LOCATION: (5)..(5)
<223> OTHER INFORMATION: X4 is selected from the group consisting of:
      Tyr (Y), Gly (G), Ala (A), Val (V), Leu (L), Ile (I), Ser (S), Thr
      (T), Cys (C), Gln (Q) and Asn (N).

<400> SEQUENCE: 37

Xaa Xaa Trp Xaa Xaa
1               5

<210> SEQ ID NO 38
<211> LENGTH: 6
<212> TYPE: PRT
<213> ORGANISM: Artificial sequence
<220> FEATURE:
<223> OTHER INFORMATION: Peptide
<220> FEATURE:
<221> NAME/KEY: X1
<222> LOCATION: (1)..(1)
<223> OTHER INFORMATION: X1 is selected from the group consisting of:
      His (H), Arg (R), Lys (K), Gly (G), Ala (A), Val (V), Leu (L), Ile
      (I), Ser (S), Thr (T), Cys (C), Asn (N) and Gln (Q).
<220> FEATURE:
<221> NAME/KEY: X2
<222> LOCATION: (2)..(2)
<223> OTHER INFORMATION: X2 is selected from the group consisting of:
      Lys (K), dLys (dK), Arg (R), Gly (G), Ala (A), Val (V), Leu (L),
      Ile (I), Ser (S), Thr (T), Cys (C), Gln (Q), Asn (N), Glu (E) and
      Asp (D).
<220> FEATURE:
<221> NAME/KEY: X3
<222> LOCATION: (4)..(4)
<223> OTHER INFORMATION: X3 is selected from the group consisting of:
      Phe (F), Tyr (Y), Trp (W), Gly (G), Ala (A), Val (V), Leu (L), Ile
      (I), Ser (S), Thr (T), Cys (C), Met (M), Asn (N), Gln (Q), Glu (E)
      and Asp (D).
<220> FEATURE:
<221> NAME/KEY: X4
<222> LOCATION: (5)..(5)
<223> OTHER INFORMATION: X4 is selected from the group consisting of:
      Tyr (Y), Gly (G), Ala (A), Val (V), Leu (L), Ile (I), Ser (S), Thr
      (T), Cys (C), Gln (Q) and Asn (N).
<220> FEATURE:
<221> NAME/KEY: X5
<222> LOCATION: (6)..(6)
<223> OTHER INFORMATION: X5 is selected from the group consisting of:
      Gly (G), Ala (A), Val (V), Leu (L), Ile (I), Ser (S), Thr (T), Cys
      (C), Phe (F), Tyr (Y), Trp (W), Met (M), Lys (K) and Arg (R).
```

```
<400> SEQUENCE: 38

Xaa Xaa Trp Xaa Xaa Xaa
1               5

<210> SEQ ID NO 39
<211> LENGTH: 5
<212> TYPE: PRT
<213> ORGANISM: Artificial sequence
<220> FEATURE:
<223> OTHER INFORMATION: Peptide
<220> FEATURE:
<221> NAME/KEY: X2
<222> LOCATION: (1)..(1)
<223> OTHER INFORMATION: X2 is selected from the group consisting of:
      Lys, d-Lys, Arg, Gly, Ala, Val, Leu, Ile, Ser, Thr, Cys, Gln, Asn,
      Glu and Asp.
<220> FEATURE:
<221> NAME/KEY: X3
<222> LOCATION: (3)..(3)
<223> OTHER INFORMATION: X3 is selected from the group consisting of:
      Phe, Tyr, Trp, Gly, Ala, Val, Leu, Ile, Ser, Thr, Cys, Met, Asn,
      Gln, Glu and Asp.
<220> FEATURE:
<221> NAME/KEY: X4
<222> LOCATION: (4)..(4)
<223> OTHER INFORMATION: X4 is selected from the group consisting of:
      Tyr, Gly, Ala, Val, Leu, Ile, Ser, Thr, Cys, Gln, Asn and dAsn.
<220> FEATURE:
<221> NAME/KEY: X5
<222> LOCATION: (5)..(5)
<223> OTHER INFORMATION: X5 is selected from the group consisting of:
      Gly, Ala, Val, Leu, Ile, Ser, Thr, Cys, Phe, Tyr, Trp, Met, Lys
      and Arg.

<400> SEQUENCE: 39

Xaa Trp Xaa Xaa Xaa
1               5

<210> SEQ ID NO 40
<211> LENGTH: 5
<212> TYPE: PRT
<213> ORGANISM: Artificial sequence
<220> FEATURE:
<223> OTHER INFORMATION: Peptide
<220> FEATURE:
<221> NAME/KEY: X1
<222> LOCATION: (1)..(1)
<223> OTHER INFORMATION: X1 is selected from the group consisting of:
      His, Arg, Lys, Gly, Ala, Val, Leu, Ile, Ser, Thr, Cys, Asn and
      Gln.
<220> FEATURE:
<221> NAME/KEY: X2
<222> LOCATION: (2)..(2)
<223> OTHER INFORMATION: X2 is selected from the group consisting of:
      Lys, d-Lys, Arg, Gly, Ala, Val, Leu, Ile, Ser, Thr, Cys, Gln, Asn,
      Glu and Asp.
<220> FEATURE:
<221> NAME/KEY: X3
<222> LOCATION: (4)..(4)
<223> OTHER INFORMATION: X3 is selected from the group consisting of:
      Phe, Tyr, Trp, Gly, Ala, Val, Leu, Ile, Ser, Thr, Cys, Met, Asn,
      Gln, Glu and Asp.
<220> FEATURE:
<221> NAME/KEY: X4
<222> LOCATION: (5)..(5)
<223> OTHER INFORMATION: X4 is selected from the group consisting of:
      Tyr, Gly, Ala, Val, Leu, Ile, Ser, Thr, Cys, Gln, Asn and dAsn.

<400> SEQUENCE: 40

Xaa Xaa Trp Xaa Xaa
1               5

<210> SEQ ID NO 41
```

```
<211> LENGTH: 5
<212> TYPE: PRT
<213> ORGANISM: Artificial sequence
<220> FEATURE:
<223> OTHER INFORMATION: Peptide
<220> FEATURE:
<221> NAME/KEY: X2-Trp-X3-X4-X5
<222> LOCATION: (1)..(5)
<223> OTHER INFORMATION: The sequences are selected from the group
      consisting of: Lys-Trp-Met-Asn-Val (SEQ ID NO: 7), Lys-Trp-Val-
      Asn-Tyr (SEQ ID NO: 8), and Lys-Trp-Phe-Val-Ala (SEQ ID NO: 9).

<400> SEQUENCE: 41

Xaa Trp Xaa Xaa Xaa
1               5

<210> SEQ ID NO 42
<211> LENGTH: 5
<212> TYPE: PRT
<213> ORGANISM: Artificial sequence
<220> FEATURE:
<223> OTHER INFORMATION: Peptide
<220> FEATURE:
<221> NAME/KEY: X1-X2-Trp-X3-X4
<222> LOCATION: (1)..(5)
<223> OTHER INFORMATION: The sequences are selected from the group
      consisting of: Arg-Lys-Trp-Phe-Val (SEQ ID NO: 10), Arg-Lys-Trp-
      Val-Asn (SEQ ID NO: 11) and Cys-Lys-Trp-Met-Asn (SEQ ID NO: 12).

<400> SEQUENCE: 42

Xaa Xaa Trp Xaa Xaa
1               5

<210> SEQ ID NO 43
<211> LENGTH: 6
<212> TYPE: PRT
<213> ORGANISM: Artificial sequence
<220> FEATURE:
<223> OTHER INFORMATION: Peptide
<220> FEATURE:
<221> NAME/KEY: X1-X2-Trp-X3-X4-X5
<222> LOCATION: (1)..(6)
<223> OTHER INFORMATION: The sequences are selected from the group
      consisting of: SEQ ID NO. 13-24.

<400> SEQUENCE: 43

Xaa Xaa Trp Xaa Xaa Xaa
1               5

<210> SEQ ID NO 44
<211> LENGTH: 8
<212> TYPE: PRT
<213> ORGANISM: Artificial sequence
<220> FEATURE:
<223> OTHER INFORMATION: Peptide
<220> FEATURE:
<221> NAME/KEY: X1
<222> LOCATION: (1)..(1)
<223> OTHER INFORMATION: X1 is selected from the group consisting of:
      His (H), Arg (R), Lys (K), Gly (G), Ala (A), Val (V), Leu (L), Ile
      (I), Ser (S), Thr (T), Cys (C), Asn (N) and Gln (Q).
<220> FEATURE:
<221> NAME/KEY: X2
<222> LOCATION: (2)..(2)
<223> OTHER INFORMATION: X2 is selected from the group consisting of:
      Lys (K), dLys (dK), Arg (R), Gly (G), Ala (A), Val (V), Leu (L),
      Ile (I), Ser (S), Thr (T), Cys (C), Gln (Q), Asn (N), Glu (E) and
      Asp (D).
<220> FEATURE:
<221> NAME/KEY: X3
<222> LOCATION: (4)..(4)
<223> OTHER INFORMATION: X3 is selected from the group consisting of:
      Phe (F), Tyr (Y), Trp (W), Gly (G), Ala (A), Val (V), Leu (L), Ile
```

```
        (I), Ser (S), Thr (T), Cys (C), Met (M), Asn (N), Gln (Q), Glu (E)
        and Asp (D).
<220> FEATURE:
<221> NAME/KEY: X4
<222> LOCATION: (5)..(5)
<223> OTHER INFORMATION: X4 is selected from the group consisting of:
        Tyr (Y), Gly (G), Ala (A), Val (V), Leu (L), Ile (I), Ser (S), Thr
        (T), Cys (C), Gln (Q) and Asn (N).
<220> FEATURE:
<221> NAME/KEY: X5
<222> LOCATION: (6)..(6)
<223> OTHER INFORMATION: X5 is selected from the group consisting of:
        Gly (G), Ala (A), Val (V), Leu (L), Ile (I), Ser (S), Thr (T), Cys
        (C), Phe (F), Tyr (Y), Trp (W), Met (M), Lys (K) and Arg (R).
<220> FEATURE:
<221> NAME/KEY: B1
<222> LOCATION: (7)..(7)
<223> OTHER INFORMATION: B1 is selected from the group consisting of:
        Gly, Ala, Val, Leu, Ile, Met, Phe, Trp and Pro.
<220> FEATURE:
<221> NAME/KEY: B2
<222> LOCATION: (8)..(8)
<223> OTHER INFORMATION: B2 is selected from the group consisting of:
        Ser, Thr, Cys, Tyr, Asn and Gln.

<400> SEQUENCE: 44

Xaa Xaa Trp Xaa Xaa Xaa Xaa Xaa
1               5

<210> SEQ ID NO 45
<211> LENGTH: 10
<212> TYPE: PRT
<213> ORGANISM: Artificial sequence
<220> FEATURE:
<223> OTHER INFORMATION: Peptide
<220> FEATURE:
<221> NAME/KEY: A1
<222> LOCATION: (1)..(1)
<223> OTHER INFORMATION: A1 is selected from the group consisting of:
        Gly, Ala, Val, Leu, Ile, Met, Phe, Trp and Pro.
<220> FEATURE:
<221> NAME/KEY: A2
<222> LOCATION: (2)..(2)
<223> OTHER INFORMATION: A2 is selected from the group consisting of:
        Gly, Ala, Val, Leu, Ile, Met, Phe, Trp, Pro, Ser, Thr, Cys, Tyr,
        Asn and Gln.
<220> FEATURE:
<221> NAME/KEY: X1
<222> LOCATION: (3)..(3)
<223> OTHER INFORMATION: X1 is selected from the group consisting of:
        His (H), Arg (R), Lys (K), Gly (G), Ala (A), Val (V), Leu (L), Ile
        (I), Ser (S), Thr (T), Cys (C), Asn (N) and Gln (Q).
<220> FEATURE:
<221> NAME/KEY: X2
<222> LOCATION: (4)..(4)
<223> OTHER INFORMATION: X2 is selected from the group consisting of:
        Lys (K), dLys (dK), Arg (R), Gly (G), Ala (A), Val (V), Leu (L),
        Ile (I), Ser (S), Thr (T), Cys (C), Gln (Q), Asn (N), Glu (E) and
        Asp (D).
<220> FEATURE:
<221> NAME/KEY: X3
<222> LOCATION: (6)..(6)
<223> OTHER INFORMATION: X3 is selected from the group consisting of:
        Phe (F), Tyr (Y), Trp (W), Gly (G), Ala (A), Val (V), Leu (L), Ile
        (I), Ser (S), Thr (T), Cys (C), Met (M), Asn (N), Gln (Q), Glu (E)
        and Asp (D).
<220> FEATURE:
<221> NAME/KEY: X4
<222> LOCATION: (7)..(7)
<223> OTHER INFORMATION: X4 is selected from the group consisting of:
        Tyr (Y), Gly (G), Ala (A), Val (V), Leu (L), Ile (I), Ser (S), Thr
        (T), Cys (C), Gln (Q) and Asn (N).
<220> FEATURE:
<221> NAME/KEY: X5
<222> LOCATION: (8)..(8)
<223> OTHER INFORMATION: X5 is selected from the group consisting of:
        Gly (G), Ala (A), Val (V), Leu (L), Ile (I), Ser (S), Thr (T), Cys
```

-continued

```
      (C), Phe (F), Tyr (Y), Trp (W), Met (M), Lys (K) and Arg (R).
<220> FEATURE:
<221> NAME/KEY: B1
<222> LOCATION: (9)..(9)
<223> OTHER INFORMATION: B1 is selected from the group consisting of:
      Gly, Ala, Val, Leu, Ile, Met, Phe, Trp and Pro.
<220> FEATURE:
<221> NAME/KEY: B2
<222> LOCATION: (10)..(10)
<223> OTHER INFORMATION: B2 is selected from the group consisting of:
      Ser, Thr, Cys, Tyr, Asn and Gln.

<400> SEQUENCE: 45

Xaa Xaa Xaa Xaa Trp Xaa Xaa Xaa Xaa Xaa
1               5                   10

<210> SEQ ID NO 46
<211> LENGTH: 10
<212> TYPE: PRT
<213> ORGANISM: Artificial sequence
<220> FEATURE:
<223> OTHER INFORMATION: Peptide
<220> FEATURE:
<221> NAME/KEY: X1
<222> LOCATION: (1)..(1)
<223> OTHER INFORMATION: X1 is selected from the group consisting of:
      His (H), Arg (R), Lys (K), Gly (G), Ala (A), Val (V), Leu (L), Ile
      (I), Ser (S), Thr (T), Cys (C), Asn (N) and Gln (Q).
<220> FEATURE:
<221> NAME/KEY: X2
<222> LOCATION: (2)..(2)
<223> OTHER INFORMATION: X2 is selected from the group consisting of:
      Lys (K), dLys (dK), Arg (R), Gly (G), Ala (A), Val (V), Leu (L),
      Ile (I), Ser (S), Thr (T), Cys (C), Gln (Q), Asn (N), Glu (E) and
      Asp (D).
<220> FEATURE:
<221> NAME/KEY: X3
<222> LOCATION: (4)..(4)
<223> OTHER INFORMATION: X3 is selected from the group consisting of:
      Phe (F), Tyr (Y), Trp (W), Gly (G), Ala (A), Val (V), Leu (L), Ile
      (I), Ser (S), Thr (T), Cys (C), Met (M), Asn (N), Gln (Q), Glu (E)
      and Asp (D).
<220> FEATURE:
<221> NAME/KEY: X4
<222> LOCATION: (5)..(5)
<223> OTHER INFORMATION: X4 is selected from the group consisting of:
      Tyr (Y), Gly (G), Ala (A), Val (V), Leu (L), Ile (I), Ser (S), Thr
      (T), Cys (C), Gln (Q) and Asn (N).
<220> FEATURE:
<221> NAME/KEY: X5
<222> LOCATION: (6)..(6)
<223> OTHER INFORMATION: X5 is selected from the group consisting of:
      Gly (G), Ala (A), Val (V), Leu (L), Ile (I), Ser (S), Thr (T), Cys
      (C), Phe (F), Tyr (Y), Trp (W), Met (M), Lys (K) and Arg (R).
<220> FEATURE:
<221> NAME/KEY: B1
<222> LOCATION: (7)..(7)
<223> OTHER INFORMATION: B1 is selected from the group consisting of:
      Gly, Ala, Val, Leu, Ile, Met, Phe, Trp and Pro.
<220> FEATURE:
<221> NAME/KEY: B2
<222> LOCATION: (8)..(8)
<223> OTHER INFORMATION: B2 is selected from the group consisting of:
      Ser, Thr, Cys, Tyr, Asn and Gln.
<220> FEATURE:
<221> NAME/KEY: B3
<222> LOCATION: (9)..(9)
<223> OTHER INFORMATION: B3 is selected from the group consisting of:
      Gly, Ala, Val, Leu, Ile, Met, Phe, Trp and Pro.
<220> FEATURE:
<221> NAME/KEY: B4
<222> LOCATION: (10)..(10)
<223> OTHER INFORMATION: B4 is selected from the group consisting of:
      Ser, Thr, Cys, Tyr, Asn and Gln.

<400> SEQUENCE: 46
```

Xaa Xaa Trp Xaa Xaa Xaa Xaa Xaa Xaa Xaa
1               5                   10

<210> SEQ ID NO 47
<211> LENGTH: 12
<212> TYPE: PRT
<213> ORGANISM: Artificial sequence
<220> FEATURE:
<223> OTHER INFORMATION: Peptide
<220> FEATURE:
<221> NAME/KEY: A1
<222> LOCATION: (1)..(1)
<223> OTHER INFORMATION: A1 is absent or selected from the group
      consisting of: Gly, Ala, Val, Leu, Ile, Met, Phe, Trp and Pro.
<220> FEATURE:
<221> NAME/KEY: A2
<222> LOCATION: (2)..(2)
<223> OTHER INFORMATION: A2 is selected from the group consisting of:
      Gly, Ala, Val, Leu, Ile, Met, Phe, Trp, Pro, Ser, Thr, Cys, Tyr,
      Asn and Gln.
<220> FEATURE:
<221> NAME/KEY: X1
<222> LOCATION: (3)..(3)
<223> OTHER INFORMATION: X1 is selected from the group consisting of:
      His (H), Arg (R), Lys (K), Gly (G), Ala (A), Val (V), Leu (L), Ile
      (I), Ser (S), Thr (T), Cys (C), Asn (N) and Gln (Q).
<220> FEATURE:
<221> NAME/KEY: X2
<222> LOCATION: (4)..(4)
<223> OTHER INFORMATION: X2 is selected from the group consisting of:
      Lys (K), dLys (dK), Arg (R), Gly (G), Ala (A), Val (V), Leu (L),
      Ile (I), Ser (S), Thr (T), Cys (C), Gln (Q), Asn (N), Glu (E) and
      Asp (D).
<220> FEATURE:
<221> NAME/KEY: X3
<222> LOCATION: (6)..(6)
<223> OTHER INFORMATION: X3 is selected from the group consisting of:
      Phe (F), Tyr (Y), Trp (W), Gly (G), Ala (A), Val (V), Leu (L), Ile
      (I), Ser (S), Thr (T), Cys (C), Met (M), Asn (N), Gln (Q), Glu (E)
      and Asp (D).
<220> FEATURE:
<221> NAME/KEY: X4
<222> LOCATION: (7)..(7)
<223> OTHER INFORMATION: X4 is selected from the group consisting of:
      Tyr (Y), Gly (G), Ala (A), Val (V), Leu (L), Ile (I), Ser (S), Thr
      (T), Cys (C), Gln (Q) and Asn (N).
<220> FEATURE:
<221> NAME/KEY: X5
<222> LOCATION: (8)..(8)
<223> OTHER INFORMATION: X5 is selected from the group consisting of:
      Gly (G), Ala (A), Val (V), Leu (L), Ile (I), Ser (S), Thr (T), Cys
      (C), Phe (F), Tyr (Y), Trp (W), Met (M), Lys (K) and Arg (R).
<220> FEATURE:
<221> NAME/KEY: B1
<222> LOCATION: (9)..(9)
<223> OTHER INFORMATION: B1 is selected from the group consisting of:
      Gly, Ala, Val, Leu, Ile, Met, Phe, Trp and Pro.
<220> FEATURE:
<221> NAME/KEY: B2
<222> LOCATION: (10)..(10)
<223> OTHER INFORMATION: B2 is selected from the group consisting of:
      Ser, Thr, Cys, Tyr, Asn and Gln.
<220> FEATURE:
<221> NAME/KEY: B3
<222> LOCATION: (11)..(11)
<223> OTHER INFORMATION: B3 is selected from the group consisting of:
      Gly, Ala, Val, Leu, Ile, Met, Phe, Trp and Pro.
<220> FEATURE:
<221> NAME/KEY: B4
<222> LOCATION: (12)..(12)
<223> OTHER INFORMATION: B4 is selected from the group consisting of:
      Ser, Thr, Cys, Tyr, Asn and Gln.

<400> SEQUENCE: 47

Xaa Xaa Xaa Xaa Trp Xaa Xaa Xaa Xaa Xaa Xaa Xaa
1               5                   10

What is claimed is:

1. A peptide compound consisting of the amino acid sequence selected from the group of Arg-Lys-Trp-Phe-Val-Ala (SEQ ID NO: 13), Arg-Lys-Trp-Val-Asn-Tyr (SEQ ID NO: 14), Cys-Lys-Trp-Met-Asn-Val (SEQ ID NO: 15), Cys-Lys-Trp-Ala-Asn-Val (SEQ ID NO: 18), Cys-dLys-Trp-Met-dAsn-Val (SEQ ID NO: 20), Arg-Thr-Trp-Glu-Asn-Val (SEQ ID NO: 21), Asn-Gln-Trp-Leu-Ser-Ala (SEQ ID NO: 22), Thr-Glu-Trp-Leu-Asn-Met (SEQ ID NO: 23) and Asn-Gln-Trp-Leu-Ser-Arg (SEQ ID NO: 24).

2. A pharmaceutical composition, comprising a peptide compound of claim 1, and a pharmaceutically acceptable excipient or carrier.

3. The compositions of claim 2, which further comprises a second active agent.

4. The compositions of claim 2, wherein the second active agent is a Platelet aggregation inhibitor.

5. The composition of claim 2, wherein the second active agent is heparin, aspirin, ticlopidine, clopidogrel, abciximab, tirofiban, eptifibatide, dipyrimamole or cilostazol or a mixture thereof.

6. The composition of claim 2, which can be administered systemically or topically.

7. The composition of claim 2, which can be used by intravenous, intramuscular, intrastemal injection, intravitreal injection, infusion, inhalation, transdermal administration, oral administration, rectal administration and intra-operative instillation.

8. A method for inhibiting platelet aggregation, comprising administering an effective amount of a peptide compound of claim 1 or a pharmaceutical composition of claim 2 to a subject in need of such treatment.

9. The method of claim 8, wherein the platelet aggregation is collagen-induced aggregation.

10. The method of claim 8, wherein the platelet aggregation is caused by interacting with GPVI.

11. A method for treating thrombogenic diseases, comprising administering an effective amount of a peptide compound of claim 1 or a pharmaceutical composition of claim 2 to a subject in need of such treatment.

12. The method of claim 11, wherein the thrombogenic disease is thrombosis, venous thrombosis, established peripheral arterial disease, thrombophlebitis, arterial embolism, coronary and cerebral arterial thrombosis, unstable angina, myocardial infarction, stroke, cerebral embolism, renal embolism, pulmonary embolism and other embolism- or thrombosis-related afflictions produced by but not limited to procedural or surgical interventions.

13. The method of claim 11, which is for the prevention treatment of embolism or thrombosis during percutaneous coronary interventions, placement of coronary stents, coronary angioplasty, coronary endarectomy, carotid endarectomy, or due to platelet-aggregation complications related to atherosclerosis, inflammation, exposure of blood to artificial devices, drug effects.

14. A method for treating sepsis, tumor metastasis or inflammatory arthritis, comprising administering an effective amount of a peptide compound of claim 1 or a pharmaceutical composition of claim 2 to a subject in need of such treatment.

* * * * *